(12) United States Patent
Straub et al.

(10) Patent No.: US 6,395,300 B1
(45) Date of Patent: *May 28, 2002

(54) POROUS DRUG MATRICES AND METHODS OF MANUFACTURE THEREOF

(75) Inventors: Julie Straub, Winchester; Howard Bernstein, Cambridge; Donald E. Chickering, III, Framingham; Sarwat Khattak, Cambridge; Greg Randall, Stoneham, all of MA (US)

(73) Assignee: Acusphere, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/433,486

(22) Filed: Nov. 4, 1999

Related U.S. Application Data

(60) Provisional application No. 60/136,323, filed on May 27, 1999, and provisional application No. 60/158,659, filed on Oct. 8, 1999.

(51) Int. Cl.[7] .......................... A61K 9/14; A61K 47/02; B29B 9/00
(52) U.S. Cl. ............................ 424/489; 264/5
(58) Field of Search ................. 424/405, 400, 424/484, 489; 428/402; 264/5, 9, 11–13, 41

(56) References Cited

U.S. PATENT DOCUMENTS

| | | |
|---|---|---|
| 5,382,437 A | 1/1995 | Ecanow |
| 5,468,598 A | 11/1995 | Miller et al. |

(List continued on next page.)

FOREIGN PATENT DOCUMENTS

| | | |
|---|---|---|
| CA | 2 136 704 | 5/1995 |
| DE | 37 13 326 A1 | 10/1987 |
| EP | 0 655 237 A1 | 5/1995 |
| GB | 1 265 615 | 3/1972 |
| WO | WO 98/31346 A1 | 7/1998 |
| WO | WO 98/51282 A1 | 11/1998 |
| WO | WO 99/56731 A1 | 11/1999 |

OTHER PUBLICATIONS

Adeyeye & Price, "Chemical, dissolution stability and microscopic evaluation of suspensions of ibuprofen and sustained release ibuprofen–wax microspheres," *J. Microencapsul.* 14(3):357–77 (1997).

Ahn, et al., "Enhancement of bioavailability of ketoprofen using dry elixir as a novel dosage form," *Drug Dev. Ind. Pharm.* 24(7):697–701 (1998).

(List continued on next page.)

*Primary Examiner*—Edward J. Webman
(74) *Attorney, Agent, or Firm*—Holland & Knight LLP

(57) ABSTRACT

Drugs, especially low aqueous solubility drugs, are provided in a porous matrix form, preferably microparticles, which enhances dissolution of the drug in aqueous media. The drug matrices preferably are made using a process that includes (i) dissolving a drug, preferably a drug having low aqueous solubility, in a volatile solvent to form a drug solution, (ii) combining at least one pore forming agent with the drug solution to form an emulsion, suspension, or second solution, and (iii) removing the volatile solvent and pore forming agent from the emulsion, suspension, or second solution to yield the porous matrix of drug. The pore forming agent can be either a volatile liquid that is immiscible with the drug solvent or a volatile solid compound, preferably a volatile salt. In a preferred embodiment, spray drying is used to remove the solvents and the pore forming agent. The resulting porous matrix has a faster rate of dissolution following administration to a patient, as compared to non-porous matrix forms of the drug. In a preferred embodiment, microparticles of the porous drug matrix are reconstituted with an aqueous medium and administered parenterally, or processed using standard techniques into tablets or capsules for oral administration.

7 Claims, 4 Drawing Sheets

U.S. PATENT DOCUMENTS

| | | | |
|---|---|---|---|
| 5,470,583 A | 11/1995 | Na et al. |
| 5,500,331 A | 3/1996 | Czekai et al. |
| 5,510,118 A | 4/1996 | Bosch et al. |
| 5,513,803 A | 5/1996 | Czekai et al. |
| 5,518,187 A | 5/1996 | Bruno et al. |
| 5,518,738 A | 5/1996 | Eickhoff et al. |
| 5,534,270 A | 7/1996 | De Castro |
| 5,552,160 A | 9/1996 | Liversidge et al. |
| 5,560,932 A | 10/1996 | Bagchi et al. |
| 5,565,188 A | 10/1996 | Wong et al. |
| 5,569,448 A | 10/1996 | Wong et al. |
| 5,571,536 A | 11/1996 | Eickhoff et al. |
| 5,580,579 A | 12/1996 | Ruddy et al. |
| 5,587,143 A | 12/1996 | Wong |
| 5,591,456 A | 1/1997 | Franson et al. |
| 5,609,998 A | 3/1997 | Texter et al. |
| 5,622,938 A | 4/1997 | Wong |
| 5,657,931 A | 8/1997 | Nair et al. |
| 5,662,279 A | 9/1997 | Czekai et al. |
| 5,662,883 A | 9/1997 | Bagchi et al. |
| 5,665,331 A | 9/1997 | Bagchi et al. |
| 5,716,642 A | 2/1998 | Bagchi et al. |
| 5,718,919 A | 2/1998 | Ruddy et al. |
| 5,747,001 A | 5/1998 | Wiedmann et al. |
| 5,762,961 A | 6/1998 | Roser et al. |
| 5,919,434 A | 7/1999 | Dugstad et al. |
| 5,976,574 A | 11/1999 | Gordon |
| 5,985,285 A | 11/1999 | Titball et al. |
| 6,001,336 A | 12/1999 | Gordon |

OTHER PUBLICATIONS

Akade, et al., "Influence of polyethylene glycol 6000 and mannitol on the in–vitro dissolution properties of nitrofurantoin by the dispersion technique," *Pharmazie.* 41(12):849–51 (1986).

Akbarieh & Tawashi, "Morphic features of solid particles after micronization in the fluid energy mill," *Int. J. Pharm.* 35:81–89 (1987).

Akade, et al., "Influence of polyethylene glycol 6000 and mannitol on the in–vitro dissolution properties of nitrofurantoin by the dispersion technique," *Pharmazie.* 41(12):849–51 (1986).

Akbarieh & Tawashi, "Morphic features of solid particles after micronization in the fluid energy mill," *Int. J. Pharm.* 35:81–89 (1987).

Allen, et al., "Dissolution rates of corticosteroids utilizing sugar glass dispersions," *J. Pharm. Sci.* 66(4):494–97 (1977).

Appel & Zentner, "Use of modified ethylcellulose lattices for microporous coating of osmotic tablets," *Pharm. Res.* 8(5):600–04 (1991).

Arias, "Dissolution properties and in vivo behaviour of triamterene in solid dispersions with polyethylene glycols," *Pharm. Acta. Helv.* 71(4):229–35 (1996).

Arias, et al., "The application of solid dispersion technique with D–mannitol to the improvement in oral absorption of triamterene," *J. Drug Target.* 2(1):45–51 (1994).

Arteaga, et al., "Dissolution velocity of different calcium preparations used in the clinical field," *Rev. Med. Chil.* 124(11):1325–33 (1996).

Badiger, et al., "Porogens in the preparation of microporous hydrogels based on poly(ethylene oxides)," *Biomaterials* 14:1059–63 (1993).

Bodmeier & Paeratakul, "Spherical agglomerates of water-insoluble drugs," *J. Pharm. Sci.* 78(11):964–67 (1989).

Borgström, et al., "In vitro and in vivo evaluation of controlled–release and enteric–coated formulations of sodium salicylate," *Biopharm. Drug Dispos.* 5(3):261–72 (1984).

Buckton, et al., "The effect of comminution technique on the surface energy of a powder," *Int. J. Pharm.* 47:121–28 (1998).

Cardorniga, et al., "In vitro evaluation of the dissolution rate of crystalline suspensions destined to intramuscular administration," *Eur. J. Drug Metab. Pharmacokinet.* Spec No. 3:379–84 (1991).

Chaumeil, et al., "Micronization: a method of improving the bioavailability of poorly soluble drugs," *Meth. Find. Exp. Clin. Pharmacol.* 20(3):211–15 (1998).

Chen & Hao, "Factors affecting zero–order release kinetics of porous gelatin capsules," *Drug Dev. Ind. Pharm.* 24(6):557–62 (1998).

Chen & Hao, "In vitro performance of floating sustained–release capsule of verapamil," *Drug Dev. Ind. Pharm.* 24(11):1067–72 (1998).

Chiou & Riegelman, "Oral absorption of griseofulvin in dogs: increased absorption via solid dispersion in polyethylene glycol 6000," *J. Pharm. Sci.* 59(7):937–42 (1970).

Chiou & Riegelman, "Pharmaceutical applications of solid dispersion systems," *J. Pharm. Sci.* 60:1281–302 (1971).

Chiou, et al., "Enhancement of dissolution rates of poorly water–soluble drugs by crystallization in aqueous surfactant solutions I: Sulfathiazole, Prednisone, and Chloramphenicol," *J. Pharm. Sci.* 65:1702–04 (1976).

Christensen, et al., "Storage of polyvinylpyrrolidone (PVP) in tissues following long–term treatment with a PVP–containing vasopressin preparation," *Act. Med. Scand.* 204:295–98 (1978).

Corrigan & Holohan, "Amorphous spray–dried hydroflumethiazide–polyvinylpyrrolidone systems: physiochemical properties," *J. Pharm. Pharmacol.* 36(4):217–21 (1984).

De Almeida, et al., "Modeling dissolution of sparingly soluble multisized powders," *J. Pharm. Sci.* 86:726–32 (1997).

Dordunoo, et al., "Physical stability of solid dispersions containing triamterene or temazepam in polyethylene glycols," *J. Pharm. Pharmacol.* 49(4):390–96 (1997).

Dressman & Fleisher, "Mixing–tank model for predicting dissolution rate control or oral absorption," *J. Pharm. Sci.* 75(2):109–16 (1986).

Eichman & Robinson, "Mechanistic studies on effervescent–induced permeability enhancement," *Pharm. Res.* 15(6):925–30 (1998).

El–Fattah, et al., "Enhancement of dissolution rate of hydrochlorothiazide via solid dispersion," *Pharmazie.* 41(11):790–93 (1986).

Feinstein & Sciarra, "Development and evaluation of a dexamethasone timed–release aerosol formulation," *J. Pharm. Sci.* 64:408–13 (1975).

Fenimore & Loy, "Injectible dispersion of $^9$–tetrahydrocannabinol in saline using polyvinyl pyrrolidone," *J. Pharm. Pharmac.* 23:310 (1971).

Ford, "The current status of solid dispersions," *Pharm. Act. Helv.* 61:69–88 (1986).*

Freitas & Müller, "Spray–drying of solid lipid nanoparticles (SLN™)," *Eur. J. Pharm. Biopharm.* 46(2):145–51 (1998).*

Galia, et al., "Evaluation of various dissolution media for predicting in vivo performance of class I and II drugs," *Pharm. Res.* 15(5):698–705 (1998).*

Genta, et al., "Improvement of dexamethasone dissolution rate from spray–dried chitosan microspheres," *S.T.P. Pharma. Sciences* 5(3):202–07 (1995).*

Ghosh, et al., "Product development studies on the tablet formulation of ibuprofen to improve bioavailability," *Drug Dev. Ind. Pharm.* 24(5):473–77 (1998).*

Giunchedi, et al., "A swellable polymer as carbamazepine dissolution rate enhancer," *Boll Chim Farm.* 129(1):17–20 (1990).*

Grijseels, et al., "Dissolution at porous interfaces VI: Multiple pore systems," *J. Pharm. Sci.* 73(12):1771–74 (1984).*

Grijseels, et al., "Dissolution at porous interfaces VI: Pore effects in natural convection flow," *Pharmaceutisch Weekblad Scientific Edition* 5:88–94 (1983).*

Hammad & Müller, "Increasing drug solubility by means of bile salt–phosphatidylcholine–based mixed micelles," *Eur. J. Pharm. Biopharm.* 46(3):361–67 (1998).*

Hastedt & Wright, "Diffusion in porous materials above the percolation threshold," *Pharm. Res.* 7(9):893–901 (1990).*

Hirschberg, et al., "Oral absorption of CGS–20625, an insoluble drug, in dogs and man," *J. Pharmacokinet. Biopharm.* 23(1):11–23 (1995).

Hong, et al., "Accelerated oral absorption of gliclazide in human subjects from a soft gelatin capsule containing a PEG 400 suspension of gliclazide," *J. Controlled Release* 51(2–3):185–92 (1998).

Imai, et al., "Enhancement of the dissolution rates of poorly water–soluble drugs by water–soluble gelatin," *Chem. Pharm. Bull.* (Tokyo). 37(8):2251–52 (1989).

Imai, et al., "Rapidly absorbed solid oral formulations of ibuprofen using water–soluble gelatin," *J. Pharm. Pharmacol.* 42(9):615–19 (1990).

Ju, et al., "Drug release from hydrophilic matrices. 1. New scaling laws for predicting polymer and drug release based on the polymer disentanglement concentration and the diffusion layer," *J. Pharm. Sci.* 84(12):1455–63 (1995).

Kagkadis, et al., "A freeze–dried injectable form of ibuprofen: development and optimisation using response surface methodology," *PDA J. .Pharm. Sci. Technol.* 50(5):317–23 (1996).

Kai, et al., "Oral absorption improvement of poorly soluble drug using solid dispersion technique," *Chem. Pharm. Bull.* 44(3):568–71 (1996).

Kaneniwa & Watari, "Dissolution of slightly soluble drugs. I. Influence of particle size on dissolution behavior," *Chem. Pharm. Bull.* 22:1699–705 (1974).

Kaur, et al., "Comparison of polyethylene glycol and polyoxyethylene stearate as excipients for solid dispersion systems of griseofulvin and tolbutamide II: dissolution and solubility studies," *J. Pharm. Sci.* 69(11):1321–26 (1980).

Kawashima, et al., "Improvement of solubility and dissolution rate of poorly water–soluble salicylic acid by a spray–drying technique," *J. Pharm. Pharmacol.* 27(1):1–5 (1975).

Khan & Jiabi, "Preparation, characterization, and dissolution studies of ibuprofen solid dispersions using polyethylene glycol (PEG), talc, and PEG–talc as dispersion carriers," *Drug Dev. Ind. Pharm.* 24(5):455–62 (1998).

Khan, et al., "Controlled release coprecipitates: formulation considerations," *J. Control. Rel.* 37:131–41 (1995).

Kim & Yoon, "Development of digoxin dry elixir as a novel dosage form using a spray–drying technique," *J. Microencapsul.* 12(5):547–56 (1995).

Kincl, et al., "Increasing oral bioavailability of progesterone by formulation," *J. Steroid Biochem.* 9(1):83–84 (1978).

Kondo, et al., "Pharmacokinetics of a micronized, poorly water–soluble drug, HO–221, in experimental animals," *Biol. Pharm. Bull.* 16(8):796–800 (1993).

Kubo & Mizobe, "Improvement of dissolution rate and oral bioavailability of a sparingly water–soluble drug, (+/–)–5–[[2–(2–naphthalenylmethyl)–5–benzoxazolyl]–methyl]– 2, 4–thiazolidinedione, in co–ground mixture with D–mannitol," *Biol. Pharm. Bull.* 20(4):460–63 (1997).

Kubo, et al., "Enhancement of oral bioavailability and pharmacological effect of 1–(3,4–dimethoxyphenyl)–2, 3–bis(methoxycarbonyl)–4–hydroxy–6,7,8– trimethoxynaphthalene (TA–7552), a new hypocholesterolemic agent, by micronization in co–ground mixture with D–mannitol," *Biol. Pharm. Bull.* 19(5):741–47 (1996).

Lee, et al., "Mathematical modelling of the release of drug from porous, nonswelling transdermal drug–delivery devices," *IMA J. Math. Appl. Med. Biol.* 15(2):135–63 (1998).

Lemos–Senna, et al., "Evaluation of the hydrophobic drug loading characteristics in nanoprecipitated amphiphillic cyclodextrin nanospheres," *Pharm. Dev. Tech.* 3:85–94 (1998).

Leucuta, et al., "The kinetics of nifefipine release from porous hydrophilic matrices and the pharmacokinetics in man," *Pharmazie* 43:845–48 (1988).

Lin, et al., "Improved oral absorption of L–365260, a poorly soluble drug," *Biopharm. Drug Dispos..* 17(1):1–15 (1996).

Lin, et al., "Preparation of enteric–coated microspheres of *Mycoplasma hyopneumoniae* vaccine with cellulose acetate phthalate: (II). Effect of temperature and pH on the stability and release behaviour of microspheres," *J. Microencapsul.* 8(4):537–45 (1991).

Martindale, The Extra Pharmacopoeia, 711 Dissolution, pp. 1791–92, 30th Ed. (The Pharmaceutical Press, London 1993).

Mason & Winer, "Kinetics of aspirin, salicylic acid, and salicyluric acid following oral administration of aspirin as a tablet and two buffered solutions," *J. Pharm. Sci.* 70(3):262–65 (1981).

Migliaresi, et al., "Physical characterization of microporous poly(2–hydroxyethyl methacrylate) gels," *J. Biomed. Mater. Res.* 15:307–17 (1981).

Mishra & Yalkowsky, "A flat circular hole device for zero-order release of drugs: characterization of the moving dissolution boundary," *Pharm. Res.* 7(11):1195–97 (1990).

Morris, et al., "Structural properties of polyethylene glycol–polysorbate 80 mixture, a solid dispersion vehicle," *J. Pharm. Sci.* 81(12):1185–88 (1992).

Najib, et al., "The adsorption of hydrophilic polymers at the liquid–solid interface," *J. Pharm. Pharmac.* 29:43P (1977).

Nishimura, et al., "Dosage form design for improvement of bioavailability of levodopa VI: formulation of efferevescent enteric–coated tablets," *J. Pharm Sci.* 73(7):942–46 (1984).

Nyström, et al., "Dissolution rate measurements of sparingly soluble compounds with the Coulter Counter model TAII," *J. Pharm. Pharmacol.* 37(4):217–21 (1985).

Nyströ m & Westerberg, "The use of ordered mixtures for improving the dissolution rate of low solubility compounds," *J. Pharm. Pharmacol.* 38(3):161–65 (1986).

Otsuka, et al., "Hygroscopic stability and dissolution properties of spray–dried solid dispersions of furosemide with Eudragit," *J. Pharm. Sci.* 82(1):32–38 (1993).

Pace, et al., "Novel injectable formulations of insoluble drugs," *Pharmaceutical Technology* 116–34 (1999).

Pillay & Fassihi, "A new method for dissolution studies of lipid–filled capsules employing nifedipine as a model drug," *Pharm. Res.* 16(2):333–37 (Mar. 1999).

Reddy, et al., "Dissolution characteristics and oral absorption of digitoxin and digoxin coprecipitates," *J. Pharm. Sci.* 65(12):1753–58 (1976).

Ridolfo, et al., "Benoxaprofen, a new anti–inflammatory agent: particle–size effect on dissolution rate and oral absorption in humans," *J. Pharm. Sci.* 68(7):850–52 (1979).

Roland & Paeratakul, "Spherical Agglomerates of WaterInsoluble Drugs," *J. Pharma. Sci.* 78(11):964–67 (1989).

Saano, et al., "Relative pharmacokinetics of three oral 400 mg ibuprofen dosage forms in healthy volunteers," *Int. J. Clin. Pharm. Ther. Toxic.* 29:381–85 (1991).

Schröder & Sabel, "Nanoparticles, a drug carrier system to pass the blood–brain barrier, permit central analgesic effects of i.v. dalargin injections," *Brain Research* 710:121–24 (1996).

Serajuddin, et al., "Improved dissolution of a poorly water–soluble drug from solid dispersions in polyethylene glycol: polysorbate 80 mixtures," *J. Pharm. Sci.* 79(5):463–64 (1990).

Serajuddin, et al., "Effects of vehicle amphiphilicity on the dissolution and bioavailability of a poorly water–soluble drug from solid dispersions," *J. Pharm. Sci.* 77(5):414–17 (1988).

Serajuddin, et al., "Water migration from soft gelatin capsule shell to fill material and its effect on drug solubility," *J. Pharm. Sci.* 75(1):62–64 (1986).

Suzuki & Sunada, "Comparison of nicotinamide, ethylurea, and polyethylene glycol as carriers for nifedipine solid dispersion systems," *Chem. Pharm. Bull.* 45:1688–93 (1997).

Suzuki & Sunada, "Influence of water–soluble polymers on the dissolution of nifedipine solid dispersions with combined carriers," *Chem. Pharm. Bull.* 46:482–87 (1998).

Sweetana & Akers, "Solubility principles and practices for parenteral drug dosage form development," *PDA J. Pharm. Sci. Technol.* 50(5):330–42 (1996).

Takenaka, et al., "Preparations of solid particulates of theophylline—ethylenediamine complex by a spray–drying technique," *J. Pharm. Sci.* 71(8):914–19 (1982).

Takeuchi, et al., "Enhancement of the dissolution rate of a poorly water–soluble drug (tolbutamide) by a spray–drying solvent deposition method and disintegrants," *J. Pharm. Pharmacol.* 39(10):769–73 (1987).

Tasic, et al., "The influence of beta–cyclodextrin on the solubility and dissolution rate of paracetamol solid dispersions," *J. Pharm. Pharmacol.* 44(1):52–55 (1992).

Tingstad, et al., "Dissolution rate studies. III. Effect of type and intensity of agitation on dissolution rate," *J. Pharm. Sci.* 62(2):293–97 (1973).

Torrado, et al., "Egg albumin microspheres containing paracetamol for oral administration. I. In vitro characterization," *J. Microencapsul.* 7(4):463–70 (1990).

Velaz, et al., "Effect of PEG 4000 on the dissolution rate of naproxen," *Eur. J. Drug Metab. Pharmacokinet.* 23(2):103–08 (1998).

Venkataram & Rogers, "Characteristics of drug–phospholipid coprecipitates I: Physical properties and dissolution behavior of griseofulvin–dimyristoylphosphatidylcholine systems," *J. Pharm. Sci.* 73(6):757–61 (1984).

Vudathala & Rogers, "Dissolution of fludrocortisone from phospholipid coprecipitates," *J. Pharm. Sci.* 81(3):282–86 (1992).

Wan, et al., "Plasticizers and their effects on microencapsulation process by spray–drying in an aqueous system," *J. Microencapsul.* 9(1):53–62 (1992).

Westerberg, et al., "Physicochemical aspects of drug release. IV. The effect of carrier particle properties on the dissolution rate from ordered mixtures," *Int. J. Pharm.* 28:23–31 (1986).

Yamaoka, et al., "Comparison of body distribution of poly-(vinyl alcohol) with other water–soluble polymers after intravenous administration," *J. Pharm. Pharmacol.* 47:479–86 (1995).

Yamaoka, et al., "Fate of water–soluble polymers administered via different routes," *J. Pharm. Sci.* 84(3):349–54 (1995).

* cited by examiner

POROUS DRUG MATRICES AND METHODS OF MANUFACTURE THEREOF

CROSS-REFERENCE TO RELATED APPLICATIONS

Priority is claimed to U.S. provisional applications Ser. No. 60/136,323, filed May 27, 1999, and Ser. No. 60/158,659, filed Oct. 8, 1999.

BACKGROUND OF THE INVENTION

This invention generally relates to formulations of drugs, especially drugs having low solubility, and more particularly to methods of making formulations of such drugs to enhance their rate of dissolution.

The bioavailability of a drug can be limited by poor dissolution of the drug into aqueous bodily fluids following administration. This rate-limiting step may therefore be critical to rapidly attaining therapeutically effective drug levels.

Traditional approaches to parenteral delivery of poorly soluble drugs include using large volumes of aqueous diluents, solubilizing agents, detergents, non-aqueous solvents, or non-physiological pH solutions. These formulations, however, can increase the systemic toxicity of the drug composition or damage body tissues at the site of administration.

Other approaches have focused on the physical form of the drug itself. Since the dissolution rate of a drug particle is directly related to its surface area available to contact the aqueous media at the site of administration or site of absorption, methods of preparing drugs in nanoparticulate form have been developed in an effort to maximize the drug surface area, as described, for example, in U.S. Pat. No. 5,534,270 to De Castro and U.S. Pat. No. 5,587,143 to Wong. Nanoparticles, however, can be difficult to produce and maintain in a stable form due to the tendency of the nanoparticles to flocculate or agglomerate, particularly without the presence of surface modifying agents adsorbed or coated onto the particles. Furthermore, milling or wet grinding techniques, which are typically employed for nanonization, can be undesirable, as it can take several days to process a single batch, scaling-up of the milling or grinding process can be difficult and/or costly, the process can be difficult to conduct aseptically, and it is difficult to eliminate shedding of milling media into the product.

Other efforts directed at enhancing the rate of dissolution have focused on delivering the drug as a dispersion in a water-soluble or biodegradable matrix, typically in the form of polymeric microparticles. For example, the dissolution rate of dexamethasone reportedly was improved by entrapping the drug in chitosan microspheres made by spray-drying (Genta, et al., *S.T.P. Pharma Sciences* 5(3):202–07 (1995)). Similarly, others have reported enhanced dissolution rates by mixing a poorly soluble drug powder with a water-soluble gelatin, which purportedly makes the surface of the drug hydrophilic (Imai, et al., *J Pharm. Pharmacol*, 42:615–19 (1990)).

Related efforts have been directed to forming relatively large, porous matrices of low solubility drugs. For example, Roland & Paeratakul,"Spherical Agglomerates of Water-Insoluble Drugs," *J Pharma. Sci.*, 78(11):964–67 (1989) discloses preparing beads having a low solubility drug content up to 98%, wherein the beads have a porous internal structure. Such large beads, however, are unsuitable for parenteral administration, and the beads have less surface area and slower dissolution rates than smaller particles.

It is therefore an object of the present invention to provide compositions enhancing the dissolution rate of drugs, especially drugs having low aqueous solubility, and to provide methods of making such compositions.

It is another object of the present invention to provide compositions providing enhanced dissolution of drugs, especially drugs of low aqueous solubility, in a formulation suitable for administration by a variety of routes, including, but not limited to, parenteral, mucosal, oral, and topical administration, for local, regional, or systemic effect.

It is further object of the present invention to provide compositions for administration as a bolus injection instead of by infusion.

SUMMARY OF THE INVENTION

Drugs are provided in a porous matrix form wherein the dissolution rate of the drug is enhanced when the matrix is contacted with an aqueous medium. In a preferred embodiment, low aqueous solubility drugs are provided in a porous matrix form which forms microparticles when the matrix is contacted with an aqueous medium. The porous matrix with low aqueous solubility drugs yields upon contact with an aqueous medium microparticles having a mean diameter between about 0.1 and 5 $\mu$m and a total surface area greater than about 0.9 $m^2$/mL. The dry porous matrix is in a dry powder form having a TAP density less than or equal to 1.0 g/mL and/or having a total surface area (sum of internal and external surface area) of greater than or equal to 0.2 $m^2$/g. The porous matrices that contain the drug are preferably made using a process that includes (i) dissolving a drug in a volatile solvent to form a drug solution, (ii) combining at least one pore forming agent with the drug solution to form an emulsion, suspension, or second solution, and (iii) removing the volatile solvent and pore forming agent from the emulsion, suspension, or second solution to yield the dry porous matrix of drug. The resulting porous matrix has a faster rate of dissolution following administration to a patient, as compared to non-porous matrix forms of the drug. The pore forming agent can be either a volatile liquid that is immiscible with the drug solvent or a volatile solid compound, preferably a volatile salt. If the pore forming agent is a liquid, the agent is emulsified with the drug solution. If the pore forming agent is a solid, the agent is (i) dissolved in the drug solution, (ii) dissolved in a solvent that is not miscible in the drug solvent and then emulsified with the drug solutions or iii suspended as solid particulates in the drug solution. Optionally, hydrophilic excipients, wetting agents, and/or tonicity agents may be added to the drug solvent, the pore forming agent solvent, or both. The solution, emulsion, or suspension of the pore forming agent in the drug solution is then processed to remove the drug solvent and the pore forming agent, as well as any pore forming agent solvent. In a preferred embodiment, spray drying, optionally followed by lyophilization, fluid bed drying, or vacuum drying, is used to remove the solvents and the pore forming agent.

An advantage of the formulations is that they can be administered as a bolus, when the drug normally must be infused to avoid precipitation of the drug. By avoiding precipitation of drug in vivo, the formulations can also be administered parenterally. An additional advantage is the formulations can be administered in reduced volumes.

In one embodiment, the matrix further includes a pegylated excipient, such as pegylated phospholipid, with the drug. The pegylated excipient shields the drug from macrophage uptake, which prolong its half-life or enhance bioavailability of the drug.

In a preferred embodiment, the porous drug matrix is reconstituted with an aqueous medium and administered parenterally, such as intramuscularly, isubcutaneously, or intravenously. Alternatively, the porous drug matrix can be further processed using standard techniques into tablets or capsules for oral administration or into rectal suppositories, delivered using a dry powder inhaler for pulmonary administration, or mixed/processed into a cream or ointment for topical administration.

DETAILED DESCRIPTION OF THE INVENTION

Figure 1:
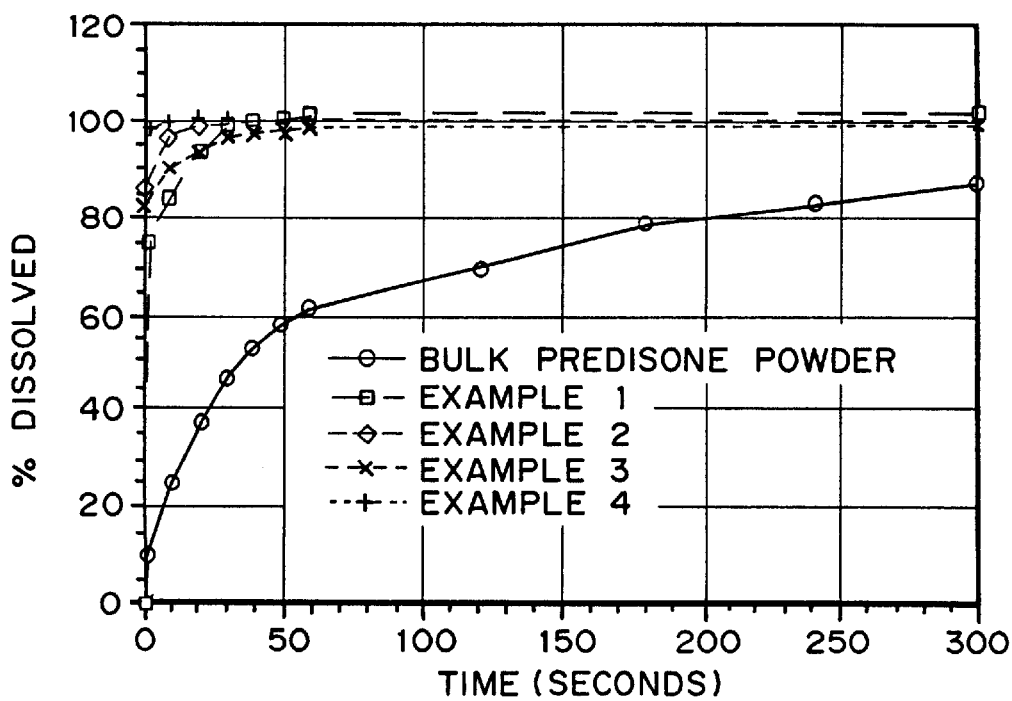
FIG. 1 is a graph of the in vitro dissolution rate (percent dissolved versus time) for non-formulated prednisone and prednisone in porous matrix form.
Figure 2:
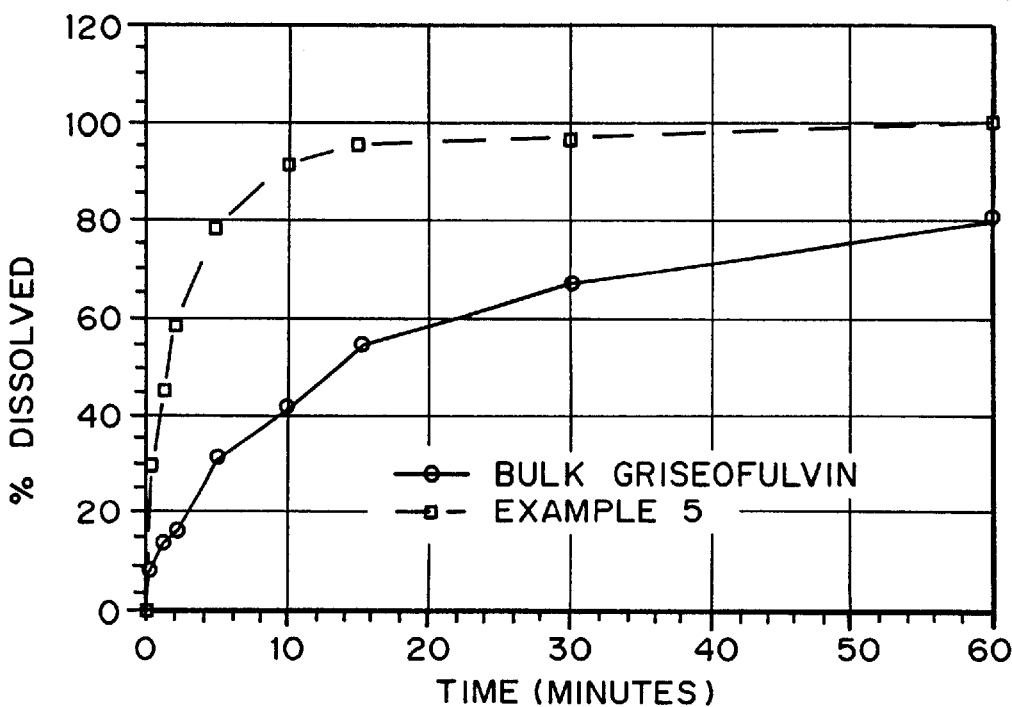
FIG. 2 is a graph of the in vitro dissolution rate (percent dissolved versus time) for non-formulated griseofulvin and griseofulvin in porous matrix form.
Figure 3:
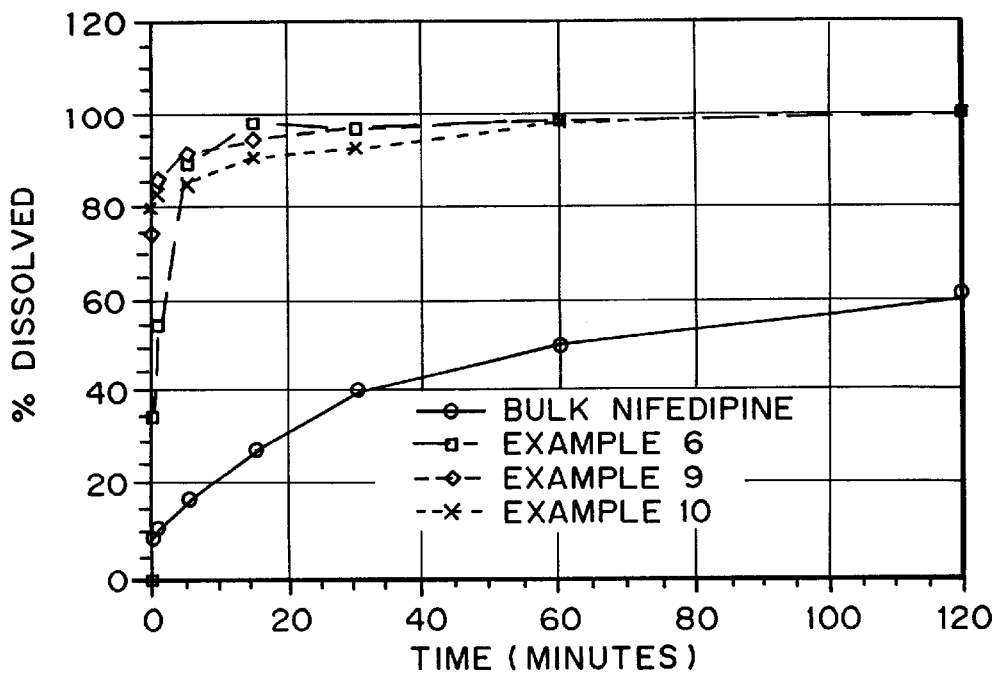
FIG. 3 is a graph of the in vitro dissolution rate (percent dissolved versus time) for non-formulated nifedipine and nifedipine in porous matrix form.
Figure 4:
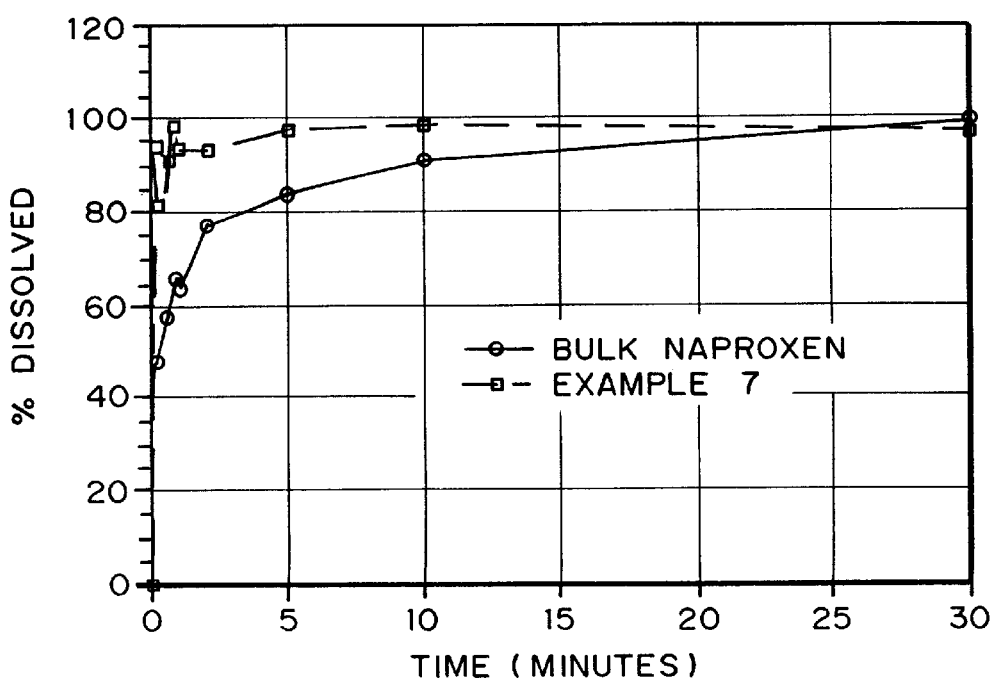
FIG. 4 is a graph of the in vitro dissolution rate (percent dissolved versus time) for non-formulated naproxen and naproxen in a porous matrix form.
Figure 5:
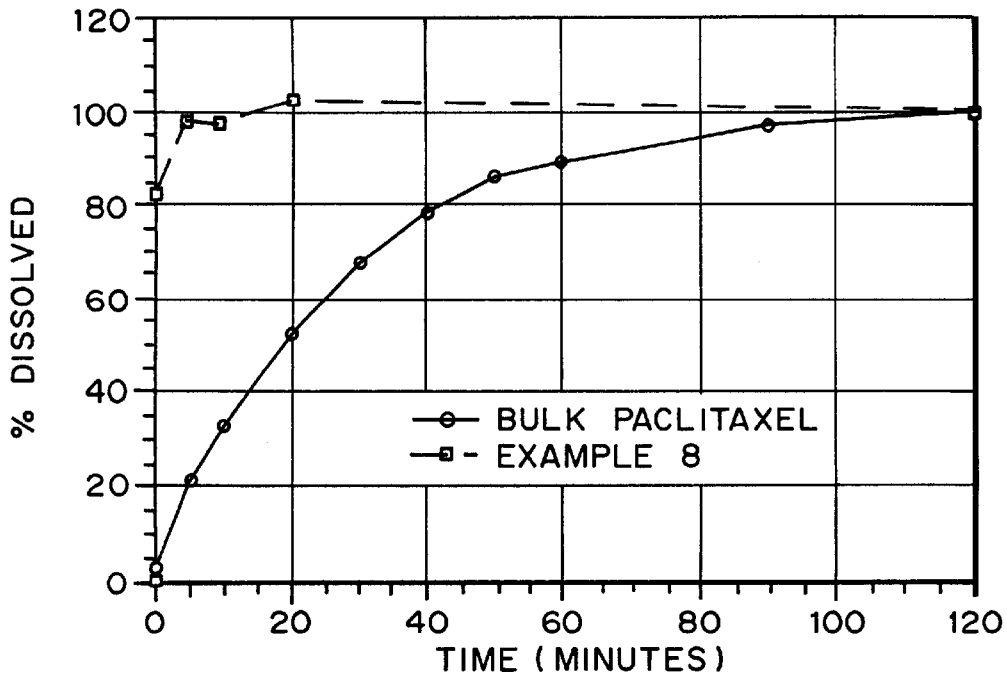
FIG. 5 is a graph of the in vitro dissolution rate (percent dissolved versus time) for non-formulated paclitaxel and paclitaxel in a porous matrix form.

The rate of dissolution of drugs can be enhanced by making the drug into a porous matrix form, substantially increasing the surface area of the drug available to contact aqueous biological fluids at the site of administration of the drug composition. In a preferred embodiment, the drug has low aqueous solubility.

I. Drug Matrix Compositions

The porous drug matrix is at least 1 to 95%, preferably at least about 10%, and more preferably between about 10 and 60%, drug by weight. The matrices also may contain hydrophilic excipients such as water soluble polymers or sugars, wetting agents such as surfactants, and tonicity agents.

The form of the drug matrix (drug powder) is critical to the dissolution rate. The matrix must contain microparticles of drug, which preferably have a diameter between about 100 nm and 5 μm, more preferably between about 500 nm and 5 μm. The average total surface area of the microparticles contained within the porous matrix, which typically is in the form of a dry powder, is 0.9 $m^2/mL$ or greater. Total surface area values can be determined using standard Coulter Counter equipment and techniques.

The drug matrix must be sufficiently porous to yield microparticles having these parameters. Measurements useful in characterizing the porosity of the drug matrix are the bulk density or the transaxial pressure ("TAP") density of the dry porous matrix (dry powder) and the total surface area (sum of internal and external surface area) of the dry porous matrix. The TAP density preferably is less than about 1.0 g/ml, more preferably less than 0.8 g/ml. This level of porosity of the matrix, characterized by density, provides sufficient surface area to enhance wetting of the dry porous matrix and enhance drug dissolution. The total surface area of the porous matrix can be measured, for example, by BET surface area analysis. The total surface area of the porous matrix preferably is greater than 0.1 $m^2/g$, more preferably greater than or equal to 0.2 $m^2/g$. This level of total surface area provides sufficient surface area to enhance wetting of the dry porous matrix and enhance drug dissolution.

1. Drugs

A wide variety drugs are useful in the methods and compositions described herein. In a preferred embodiment, the drug is a low aqueous solubility drug. As used herein, the term "low aqueous solubility" means that the drug has a solubility of less than about 10 mg/mL, and preferably less than about 5 mg/mL, in aqueous media at approximately physiological temperatures and pH. As used herein, the term "drug" refers to chemical or biological molecules providing a therapeutic, diagnostic, or prophylactic effect in vivo.

Drugs contemplated for use in the compositions described herein include the following categories and examples of drugs and alternative forms of these drugs such as alternative salt forms, free acid forms, free base forms, and hydrates:

analgesics/antipyretics (e.g., aspirin, acetaminophen, ibuprofen, naproxen sodium, buprenorphine, propoxyphene hydrochloride, propoxyphene napsylate, meperidine hydrochloride, hydromorphone hydrochloride, morphine, oxycodone, codeine, dihydrocodeine bitartrate, pentazocine, hydrocodone bitartrate, levorphanol, diflunisal, trolamine salicylate, nalbuphine hydrochloride, mefenamic acid, butorphanol, choline salicylate, butalbital, phenyltoloxamine citrate, diphenhydramine citrate, methotrimeprazine, cinnamedrine hydrochloride, and meprobamate);

antiasthamatics (e.g., ketotifen and traxanox);

antibiotics (e.g., neomycin, streptomycin, chloramphenicol, cephalosporin, ampicillin, penicillin, tetracycline, and ciprofloxacin);

antidepressants (e.g., nefopam, oxypertine, doxepin, amoxapine, trazodone, amitriptyline, maprotiline, phenelzine, desipramine, nortriptyline, tranylcypromine, fluoxetine, doxepin, imipramine, imipramine pamoate, isocarboxazid, trimipramine, and protriptyline);

antidiabetics (e.g., biguanides and sulfonylurea derivatives);

antifungal agents (e.g., griseofulvin, ketoconazole, itraconizole, amphotericin B, nystatin, and candicidin);

antihypertensive agents (e.g., propanolol, propafenone, oxyprenolol, nifedipine, reserpine, trimethaphan, phenoxybenzamine, pargyline hydrochloride, deserpidine, diazoxide, guanethidine monosulfate, minoxidil, rescinnamine, sodium nitroprusside, rauwolfia serpentina, alseroxylon, and phentolamine);

anti-inflammatories (e.g., (non-steroidal) indomethacin, ketoprofen, flurbiprofen, naproxen, ibuprofen, ramifenazone, piroxicam, (steroidal) cortisone, dexamethasone, fluazacort, celecoxib, rofecoxib, hydrocortisone, prednisolone, and prednisone);

antineoplastics (e.g., cyclophosphamide, actinomycin, bleomycin, daunorubicin, doxorubicin, epirubicin, mitomycin, methotrexate, fluorouracil, carboplatin, carmustine (BCNU), methyl-CCNU, cisplatin, etoposide, camptothecin and derivatives thereof, phenesterine, paclitaxel and derivatives thereof, docetaxel and derivatives thereof, vinblastine, vincristine, tamoxifen, and piposulfan);

antianxiety agents (e.g., lorazepam, buspirone, prazepam, chlordiazepoxide, oxazepam, clorazepate dipotassium, diazepam, hydroxyzine pamoate, hydroxyzine hydrochloride, alprazolam, droperidol, halazepam, chlormezanone, and dantrolene);

immunosuppressive agents (e.g., cyclosporine, azathioprine, mizoribine, and FK506 (tacrolimus));

antimigraine agents (e.g., ergotamine, propanolol, isometheptene mucate, and dichloralphenazone);

sedatives/hypnotics (e.g., barbiturates such as pentobarbital, pentobarbital, and secobarbital; and benzodiazapines such as flurazepam hydrochloride, triazolam, and midazolam);

antianginal agents (e.g., beta-adrenergic blockers; calcium channel blockers such as nifedipine, and diltiazem; and nitrates such as nitroglycerin, isosorbide dinitrate, pentaerythritol tetranitrate, and erythrityl tetranitrate);

antipsychotic agents (e.g., haloperidol, loxapine succinate, loxapine hydrochloride, thioridazine, thioridazine hydrochloride, thiothixene, fluphenazine, fluphenazine decanoate, fluphenazine enanthate, trifluoperazine, chlorpromazine, perphenazine, lithium citrate, and prochlorperazine);

antimanic agents (e.g., lithium carbonate);

antiarrhythmics (e.g., bretylium tosylate, esmolol, verapamil, amiodarone, encainide, digoxin, digitoxin, mexiletine, disopyramide phosphate, procainamide, quinidine sulfate, quinidine gluconate, quinidine polygalacturonate, flecainide acetate, tocainide, and lidocaine);

antiarthritic agents (e.g., phenylbutazone, sulindac, penicillanine, salsalate, piroxicam, azathioprine, indomethacin, meclofenamate, gold sodium thiomalate, ketoprofen, auranofin, aurothioglucose, and tolmetin sodium);

antigout agents (e.g., colchicine, and allopurinol);

anticoagulants (e.g., heparin, heparin sodium, and warfarin sodium);

thrombolytic agents (e.g., urokinase, streptokinase, and alteplase);

antifibrinolytic agents (e.g., aminocaproic acid);

hemorheologic agents (e.g., pentoxifylline);

antiplatelet agents (e.g., aspirin);

anticonvulsants (e.g., valproic acid, divalproex sodium, phenytoin, phenytoin sodium, clonazepam, primidone, phenobarbitol, carbamazepine, amobarbital sodium, methsuximide, metharbital, mephobarbital, mephenytoin, phensuximide, paramethadione, ethotoin, phenacemide, secobarbitol sodium, clorazepate dipotassium, and trimethadione);

antiparkinson agents (e.g., ethosuximide);

antihistamines/antipruritics (e.g., hydroxyzine, diphenhydramine, chlorpheniramine, brompheniramine maleate, cyproheptadine hydrochloride, terfenadine, clemastine fumarate, triprolidine, carbinoxamine, diphenylpyraline, phenindamine, azatadine, tripelennamine, dexchlorphenirarnine maleate, methdilazine, and);

agents useful for calcium regulation (e.g., calcitonin, and parathyroid hormone);

antibacterial agents (e.g., amikacin sulfate, aztreonam, chloramphenicol, chloramphenicol palirtate, ciprofloxacin, clindamycin, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, and colistin sulfate);

antiviral agents (e.g., interferon alpha, beta or gamma, zidovudine, amantadine hydrochloride, ribavirin, and acyclovir);

antimicrobials (e.g., cephalosporins such as cefazolin sodium, cephradine, cefaclor, cephapirin sodium, ceftizoxime sodium, cefoperazone sodium, cefotetan disodium, cefuroxime e azotil, cefotaxime sodium, cefadroxil monohydrate, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, and cefuroxime sodium; penicillins such as ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G procaine, methicillin sodium, and nafcillin sodium; erythromycins such as erythromycin ethylsuccinate, erythromycin, erythromycin estolate, erythromycin lactobionate, erythromycin stearate, and erythromycin ethylsuccinate; and tetracyclines such as tetracycline hydrochloride, doxycycline hyclate, and minocycline hydrochloride, azithromycin, clarithromycin)

anti-infectives (e.g., GM-CSF);

bronchodilators (e.g., sympathomimetics such as epinephrine hydrochloride, metaproterenol sulfate, terbutaline sulfate, isoetharine, isoetharine mesylate, isoetharine hydrochloride, albuterol sulfate, albuterol, bitolterolmesylate, isoproterenol hydrochloride, terbutaline sulfate, epinephrine bitartrate, metaproterenol sulfate, epinephrine, and epinephrine bitartrate; anticholinergic agents such as ipratropium bromide; xanthines such as aminophylline, dyphylline, metaproterenol sulfate, and aminophylline; mast cell stabilizers such as cromolyn sodium; inhalant corticosteroids such as beclomethasone dipropionate (BDP), and beclomethasone dipropionate monohydrate; salbutamol; ipratropium bromide; budesonide; ketotifen; salmeterol; xinafoate; terbutaline sulfate; triamcinolone; theophylline; nedocromil sodium; metaproterenol sulfate; albuterol; flunisolide; fluticasone proprionate steroidal compounds and hormones (e.g., androgens such as danazol, testosterone cypionate, fluoxymesterone, ethyltestosterone, testosterone enathate, methyltestosterone, fluoxymesterone, and testosterone cypionate; estrogens such as estradiol, estropipate, and conjugated estrogens; progestins such as methoxyprogesterone acetate, and norethindrone acetate; corticosteroids such as triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate, methylprednisolone sodium succinate, hydrocortisone sodium succinate, triamcinolone hexacetonide, hydrocortisone, hydrocortisone cypionate, prednisolone, fludrocortisone acetate, paramethasone acetate, prednisolone tebutate, prednisolone acetate, prednisolone sodium phosphate, and hydrocortisone sodium succinate; and thyroid hormones such as levothyroxine sodium);

hypoglycemic agents (e.g., human insulin, purified beef insulin, purified pork insulin, glyburide, chlorpropamide, glipizide, tolbutarnide, and tolazamide);

hypolipidemic agents (e.g., clofibrate, dextrothyroxine sodium, probucol, pravastitin, atorvastatin, lovastatin, and niacin);

proteins (e.g., DNase, alginase, superoxide dismutase, and lipase);

nucleic acids (e.g., sense or anti-sense nucleic acids encoding any therapeutically useful protein, including any of the proteins described herein);

agents useful for erythropoiesis stimulation (e.g., erythropoietin);

antiulcer/antireflux agents (e.g., famotidine, cimetidine, and ranitidine hydrochloride);

antinauseants/antiemetics (e.g., meclizine hydrochloride, nabilone, prochlorperazine, dimenhydrinate, promethazine hydrochloride, thiethylperazine, and scopolamine);

oil-soluble vitamins (e.g., vitamins A, D, E, K, and the like);

as well as other drugs such as mitotane, halonitrosoureas, anthrocyclines, and ellipticine. A description of these and other classes of useful drugs and a listing of species within each class can be found in Martindale, *The Extra Pharmacopoeia*, 30th Ed. (The Pharmaceutical Press, London 1993), the disclosure of which is incorporated herein by reference in its entirety.

Examples of other drugs useful in the compositions and methods described herein include ceftriaxone, ketoconazole, ceftazidime, oxaprozin, albuterol, valacyclovir, urofollitropin, famciclovir, flutamide, enalapril, mefformin, itraconazole, buspirone, gabapentin, fosinopril, tramadol, acarbose, lorazepan, follitropin, glipizide, omeprazole, fluoxetine, lisinopril, tramsdol, levofloxacin, zafirlukast, interferon, growth hormone, interleukin, erythropoietin, granulocyte stimulating factor, nizatidine, bupropion, perindopril, erbumine, adenosine, alendronate, alprostadil, benazepril, betaxolol, bleomycin sulfate, dexfenfluramine, diltiazem, fentanyl, flecainid, gemcitabine, glatiramer acetate, granisetron, lamivudine, mangafodipir trisodium, mesalamine, metoprolol fumarate, metronidazole, miglitol, moexipril, monteleukast, octreotide acetate, olopadaine, paricalcitol, somatropin, sumatriptan succinate, tacrine, verapamil, nabumetone, trovafloxacin, dolasetron, zidovudine, finasteride, tobramycin, isradipine, tolcapone, enoxaparin, fluconazole, lansoprazole, terbinafine, pamidronate, didanosine, diclofenac, cisapride, venlafaxine, troglitazone, fluvastatin, losartan, imiglucerase, donepezil, olanzapine, valsartan, fexofenadine, calcitonin, and ipratropium bromide. These drugs are generally considered to be water soluble.

Preferred drugs include albuterol, adapalene, doxazosin mesylate, mometasone furoate, ursodiol, amphotericin, enalapril maleate, felodipine, nefazodone hydrochloride, valrubicin, albendazole, conjugated estrogens, medroxyprogesterone acetate, nicardipine hydrochloride, zolpidem tartrate, amlodipine besylate, ethinyl estradiol, omeprazole, rubitecan, amlodipine besylate/ benazepril hydrochloride, etodolac, paroxetine hydrochloride, paclitaxel, atovaquone, felodipine, podofilox, paricalcitol, betamethasone dipropionate, fentanyl, pramipexole dihydrochloride, Vitamin $D_3$ and related analogues, finasteride, quetiapine fumarate, alprostadil, candesartan, cilexetil, fluconazole, ritonavir, busulfan, carbamazepine, flumazenil, risperidone, carbemazepine, carbidopa, levodopa, ganciclovir, saquinavir, amprenavir, carboplatin, glyburide, sertraline hydrochloride, rofecoxib carvedilol, halobetasolproprionate, sildenafil citrate, celecoxib, chlorthalidone, imiquimod, simvastatin, citalopram, ciprofloxacin, irinotecan hydrochloride, sparfloxacin, efavirenz, cisapride monohydrate, lansoprazole, tamsulosin hydrochloride, mofafinil, clarithromycin, letrozole, terbinafine hydrochloride, rosiglitazone maleate, diclofenac sodium, lomefloxacin hydrochloride, tirofiban hydrochloride, telmisartan, diazapam, loratadine, toremifene citrate, thalidomide, dinoprostone, mefloquine hydrochloride, trandolapril, docetaxel, mitoxantrone hydrochloride, tretinoin, etodolac, triamcinolone acetate, estradiol, ursodiol, nelfinavir mesylate, indinavir, beclomethasone dipropionate, oxaprozin, flutamide, famotidine, nifedipine, prednisone, cefuroxime, lorazepam, digoxin, lovastatin, griseofulvin, naproxen, ibuprofen, isotretinoin, tamoxifen citrate, nimodipine, amiodarone, and alprazolam.

2. Excipients

The matrices may contain hydrophilic excipients such as water soluble polymers or sugars which can serve as bulking agents or as wetting agents, wetting agents such as surfactants or sugars, and tonicity agents. Upon contact with an aqueous medium, water penetrates through the highly porous matrix to dissolve the water soluble excipients in the matrix. In the case of low aqueous solubility drugs, a suspension of drug particles in the aqueous medium is left. The total surface area of the resultant low aqueous solubility drug microparticles is increased relative to the unprocessed drug and the dissolution rate of the drug is increased.

One of skill in the art can select appropriate excipients for use in the drug matrix compositions, considering a variety of factors, such as the drug to be administered, the route of administration, the dosage, and the preferred dissolution rate. For example, the excipients can function as bulking agents, release-modifiers, wetting agents, tonicity agents, or combinations thereof. Preferred excipients include hydrophilic polymers, wetting agents, and sugars. The amount of excipient in the drug matrix is less than about 95%, more preferably less than about 80%, by weight of the drug matrix.

The hydrophilic excipients, wetting agents, and tonicity agents may be added to the drug solution, the pore forming agent, or both, during production of the matrix.

(i) Hydrophilic Polymers

The polymers that can be used in the drug matrices described herein include both synthetic and natural polymers, either non-biodegradable or biodegradable. Representative synthetic polymers include polyethylene glycol ("PEG"), polyvinyl pyrrolidone, polymethacrylates, polylysine, poloxamers, polyvinyl alcohol, polyacrylic acid, polyethylene oxide, and polyethyoxazoline. Representative natural polymers include albumin, alginate, gelatin, acacia, chitosan, cellulose dextran, ficoll, starch, hydroxyethyl cellulose, hydroxypropyl cellulose, hydroxy-propylmethyl cellulose, hyaluronic acid, carboxyethyl cellulose, carboxymethyl cellulose, deacetylated chitosan, dextran sulfate, and derivatives thereof. Preferred hydrophilic polymers include PEG, polyvinyl pyrrolidone, poloxamers, hydroxypropyl cellulose, and hydroxyethyl cellulose.

The hydrophilic polymer selected for use in a particular drug matrix formulation is based on a variety of factors, such as the polymer molecular weight, polymer hydrophilicity, and polymer inherent viscosity. The hydrophilic polymer can be used as a bulking agent or as a wetting agent.

(ii) Sugars

Representative sugars that can be used in the drug matrices include mannitol, sorbitol, xylitol, glucitol, ducitol, inositiol, arabinitol; arabitol, galactitol, iditol, allitol, fructose, sorbose, glucose, xylose, trehalose, allose, dextrose, altrose, gulose, idose, galactose, talose, ribose, arabinose, xylose, lyxose, sucrose, maltose, lactose, lactulose, fucose, rhamnose, melezitose, maltotriose, and raffinose. Preferred sugars include mannitol, lactose, sucrose, sorbitol, trehalose, glucose, and are adjusted to provide osmolality if administered parenterally or to provide wetting of the porous drug matrix or the drug microparticles within the matrix.

(iii) Wetting Agents

Wetting agents can be used to facilitate water ingress into the matrix and wetting of the drug particles in order to facilitate dissolution.

Representative examples of wetting agents include gelatin, casein, lecithin (phosphatides), gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., TWEEN™s), polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxy propylcellulose, hydroxypropylmethylcellulose phthlate, noncrystalline cellulose, magnesium aluminum silicate, triethanolamine, polyvinyl alcohol, and polyvinylpyrrolidone (PVP). Tyloxapol (a nonionic liquid polymer of the alkyl aryl polyether alcohol type, also known as superinone or triton) is another useful wetting agent. Most of these wetting agents are known pharmaceutical excipients and are described in detail in the Handbook of Pharmaceutical Excipients, published jointly by the American Pharmaceutical Association and The Pharmaceutical Society of Great Britain (The Pharmaceutical Press, 1986).

Preferred wetting agents include polyvinylpyrrolidone, polyethylene glycol, tyloxapol, poloxamers such as PLURONIC™ F68, F127, and F108, which are block copolymers of ethylene oxide and propylene oxide, and polyxamines such as TETRONIC™ 908 (also known as POLOXAMINE™ 908), which is a tetraflnctional block copolymer derived from sequential addition of propylene oxide and ethylene oxide to ethylenediamine (available from BASF), dextran, lecithin, dialkylesters of sodium sulfosuccinic acid such as AEROSOL™ OT, which is a dioctyl ester of sodium sulfosuccinic acid (available from American Cyanimid), DUPONOL™ P, which is a sodium lauryl sulfate (available from DuPont), TRITON™ X-200, which is an alkyl aryl polyether sulfonate (available from Rohm and Haas), TWEEN™ 20 and TWEEN™ 80, which are polyoxyethylene sorbitan fatty acid esters (available from ICI Specialty Chemicals), Carbowax 3550 and 934, which are polyethylene glycols (available from Union Carbide), Crodesta F-110, which is a mixture of sucrose stearate and sucrose distearate, and Crodesta SL-40 (both available from Croda Inc.), and SA9OHCO, which is $C_{18}H_{37}$-$CH_2$(CON($CH_3$)$CH_2$($CHOH$)$_4$$CH_2OH$)$_2$.

Wetting agents which have been found to be particularly useful include Tetronic 908, the Tweens, Pluronic F-68 and polyvinylpyrrolidone. Other useful wetting agents include decanoyl-N-methylglucamide; n-decyl-β-D-glucopyranoside; n-decyl-β-D-maltopyranoside; n-dodecyl-β-D-glucopyranoside; n-dodecyl β-D-maltoside; heptanoyl-N-methylglucamide; nheptyl-β-D-glucopyranoside; n-heptyl-β-D-thioglucoside; n-hexyl-β-D-glucopyranoside; nonanoyl-N-methylglucamide; n-noyl-,-D-glucopyranoside; octanoyl-N-methylglucamide; n-octyl-β-D-glucopyranoside; and octyl-β-D-thioglucopyranoside. Another preferred wetting agent is p-isononylphenoxypoly(glycidol), also known as Olin-10G or Surfactant 10-G (commercially available as 10G from Olin Chemicals). Two or more wetting agents can be used in combination.

(iv) Tonicity or Osmolality Agents

The porous drug matrices may include one or more tonicity agents, such as salts (e.g., as sodium chloride or potassium chloride) or sugars (such as mannitol, dextrose, sucrose, or trehalose) to adjust a hypotonic solution of a drug to isotonic so that the drug, when in solution, is physiologically compatible with the cells of the body tissue of the patient. The type and amount of tonicity agent can be selected by one of skill in the art using known techniques.

(v) PEG lated Excipients

In one embodiment, the matrix further includes a pegylated excipient. Such pegylated excipients include, but are not limited to, pegylated phospholipids, pegylated proteins, pegylated peptides, pegylated sugars, pegylated polysaccharides, pegylated block-co-polymers with one of the blocks being PEG, and pegylated hydrophobic compounds such as pegylated cholesterol. The pegylated excipient beneficially envelops or shields the drug from macrophage uptake, which prolongs its half-life or enhances bioavailability of the drug.

Representative examples of pegylated phospholipids include 1,2-diacylsn-glycero-3-phosphoethanolamine-N-[Poly(ethylene glycol) 2000] ("PEG 2000 PE") and 1,2-diacyl-sn-glycero-3-phosphoethanolamine-N-[Poly(ethylene glycol) 5000] ("PEG 5000 PE"), where the acyl group is selected, for example, from dimyristoyl, dipalmitoyl, distearoyl, diolcoyl, and 1-palmitoyl-2-oleoyl.

Other polyalkyleneoxides can be used in the place of the polyethylene glycol moiety.

II. Volatile Solvents

The choice of solvent depends on the drug. In a preferred embodiment, the solvent is an organic solvent that is volatile, has a relatively low boiling point, or can be removed under vacuum, and which is acceptable for administration to humans in trace amounts. Representative solvents include acetic acid, acetaldehyde dimethyl acetal, acetone, acetonitrile, chloroform, chlorofluorocarbons, dichloromethane, dipropyl ether, diisopropyl ether, N,N-dimethlyformamide (DMF), foramide, demethyl sulfoxide (DMSO), dioxane, ethanol, ethyl acetate, ethyl formate, ethyl vinyl ether, methyl ethyl ketone (MEK), glycerol, heptane, hexane, isopropanol, methanol, isopropanol, butanol, triethylamine, nitromethane, octane, pentane, tetrofuran (THF), toluene, 1,1,1-trichloroethane, 1,1,2-trichloroethylene, water, xlene, and combinations thereof. In general, the drug is dissolved in the volatile solvent to form a drug solution having a concentration of between 0.01 and 80% weight to volume (w/v), more preferably between 0.025 and 30% (w/v).

When the drug is a water soluble drug, aqueous solvents or mixtures of aqueous and organic solvents, such as water-alcohol mixtures, can be used to dissolve the drug.

III. Pore Forming Agents

Pore forming agents are volatile materials that are used during the process to create porosity in the resultant matrix. The pore forming agent can be a volatilizable solid or volatilizable liquid.

1. Liquid Pore Forming Agent

The liquid pore forming agent must be immiscible with the drug solvent and volatilizable under processing conditions compatible with the drug. To effect pore formation, the pore forming agent first is emulsified with the drug solvent. Then, the emulsion is further processed to remove the drug solvent and the pore forming agent simultaneously or sequentially using evaporation, vacuum drying, spray drying, fluid bed drying, lyophilization, or a combination of these techniques.

The selection of liquid pore forming agents will depend on the drug solvent. Representative liquid pore forming agents include water; dichloromethane; alcohols such as ethanol, methanol, or isopropanol; acetone; ethyl acetate; ethyl formate; dimethylsulfoxide; acetonitrile; toluene; xylene; dimethylforamide; ethers such as THF, diethyl ether, or dioxane; triethylatnine; foramide; acetic acid; methyl ethyl ketone; pyridine; hexane; pentane; furan; water; and cyclohexane.

The liquid pore forming agent is used in an amount that is between 1 and 50% (v/v), preferably between 5 and 25% (v/v), of the drug solvent emulsion.

2. Solid Pore Forming Agent

The solid pore forming agent must be volatilizable under processing conditions which do not harm the drug compositions. The solid pore forming agent can be (i) dissolved in the drug solution, (ii) dissolved in a solvent which is not miscible with the drug solvent to form a solution which is then emulsified with the drug solution, or (iii) added as solid particulates to the drug solution. The solution, emulsion, or suspension of the pore forming agent in the drug solution then is further processed to remove the drug solvent, the pore forming agent, and, if appropriate, the solvent for the pore forming agent simultaneously or sequentially using evaporation, spray drying, fluid bed drying, lyophilization, vacuum drying, or a combination of these techniques.

In a preferred embodiment, the solid pore forming agent is a volatile salt, such as salts of volatile bases combined with volatile acids. Volatile salts are materials that can transform from a solid or liquid to a gaseous state using added heat and/or vacuum. Examples of volatile bases include ammonia, methylamine, ethylamine, dimethylamine, diethylamine, methylethylamine, trimethylamine, triethylamine, and pyridine. Examples of volatile acids include carbonic acid, hydrochloric acid, hydrobromic acid, hydroiodic acid, formic acid, acetic acid, propionic acid, butyric acid, and benzoic acid. Preferred volatile salts include ammonium bicarbonate, ammonium acetate, ammonium chloride, ammonium benzoate and mixtures thereof Other examples of solid pore forming agents include iodine, phenol, benzoic acid (as acid not as salt), and naphthalene.

The solid pore forming agent is used in an amount between 5 and 1000% (w/w), preferably between 10 and 600% (w/w), and more preferably between 10 and 100% (w/w), of the drug.

IV. Method of Making the Porous Drug Matrix

The porous drug matrices preferably are made by (i) dissolving a drug, preferably one having low aqueous solubility, in a volatile solvent to form a drug solution, (ii) combining at least one pore forming agent with the drug solution to form an emulsion, suspension, or second solution, and (iii) removing the volatile solvent and pore forming agent from the emulsion, suspension, or second solution. In a preferred embodiment, spray drying, optionally followed by lyophilization or vacuum drying, is used to remove the solvents and the pore forming agent. The removal of the pore forming agent can be conducted simultaneously with or following removal of enough solvent to solidify the droplets. Production can be carried out using continuous, batch, or semicontinuous processes.

First, the selected drug is dissolved in an appropriate solvent. The concentration of the drug in the resulting drug solution typically is between about 0.01 and 80% (w/v), preferably between about 0.025 and 30% (w/v).

Next, the drug solution is combined, typically under mixing conditions, with the pore forming agent or solution thereof. If a liquid pore forming agent is used, it is first emulsified with the drug solution to form droplets of pore forming agent dispersed throughout the drug solution. If a solid pore forming agent is used, it is dissolved either directly in the drug solution to form a solution of drug/pore forming agent, or it is first dissolved in a second solvent which is immiscible with the drug solvent to form a solution which subsequently is emulsified with the drug solution to form droplets of the pore forming agent solution dispersed throughout the drug solution. A solid pore forming agent alternatively can be added directly to the drug solution as solid particulates, preferably between about 100 nm and 10 μm in size, to form a suspension of pore forming agent in the drug solution. Subsequently, the solid pore forming agent particle size can be reduced by further processing the resulting suspension, for example, using homogenization or sonication techniques known in the art.

Then, the solution, emulsion, or suspension is further processed to remove the drug solvent and the pore forming agent simultaneously or sequentially, using evaporation, spray drying, fluid bed drying, lyophilization, vacuum drying, or a combination of these techniques. In a preferred embodiment, the solution, emulsion, or suspension is spray-dried. As used herein,"spray dry" means to atomize the solution, emulsion, or suspension to form a fine mist of droplets (of drug solution having solid or liquid pore forming agent dispersed throughout), which immediately enter a drying chamber (e.g., a vessel, tank, tubing, or coil) where they contact a drying gas. The solvent and pore forming agents evaporate from the droplets into the drying gas to solidify the droplets, simultaneously forming pores throughout the solid. The solid (typically in a powder, particulate form) then is separated from the drying gas and collected.

The temperature of the inlet and outlet ports of the drying chamber, as well as the flow rates of the feed solution, atomization gas, and drying gas, can be controlled to produce the desired products. In a particularly preferred embodiment, the spray drying methods described in U.S. Pat. No. 5,853,698 to Straub et al., which is hereby incorporated by reference, are adapted to make the drug matrices described herein.

The drug present in the solids or powder produced may be in a crystalline or an amorphous state, or may be mixture of such states. The stated generally depends on how the droplets are dried and the excipients present.

Emulsion Stabilization

In embodiments in which at least one pore forming agent is combined with the drug solution to form an emulsion, a surfactant or emulsifying agent can be added to enhance the stability of the emulsion. A variety of surfactants may be incorporated in this process, preferably to an amount between 0.1 and 5% by weight. Exemplary emulsifiers or surfactants which may be used include most physiologically acceptable emulsifiers, for instance egg lecithin or soya bean lecithin, or synthetic lecithins such as saturated synthetic lecithins, for example, dimyristoyl phosphatidyl choline, dipalmitoyl phosphatidyl choline or distearoyl phosphatidyl choline or unsaturated synthetic lecithins, such as dioleyl phosphatidyl choline or dilinoleyl phosphatidyl choline. Other hydrophobic or amphipathic compounds can be used in place of the phospholipid, for example, cholesterol. Emulsifiers also include surfactants such as free fatty acids, esters of fatty acids with polyoxyalkylene compounds like polyoxpropylene glycol and polyoxyethylene glycol; ethers of fatty alcohols with polyoxyalkylene glycols; esters of fatty acids with polyoxyalkylated sorbitan; soaps; glycerol-polyalkylene stearate; glycerol-polyoxyethylene ricinoleate;

homo- and co-polymers of polyalkylene glycols; polyethoxylated soya-oil and castor oil as well as hydrogenated derivatives; ethers and esters of sucrose or other carbohydrates with fatty acids, fatty alcohols, these being optionally polyoxyalkylated; mono-, di- and tri-glycerides of saturated or unsaturated fatty acids, glycerides of soya-oil and sucrose.

Other emulsifiers include natural and synthetic forms of bile salts or bile acids, both conjugated with amino acids and unconjugated such as taurodeoxycholate and cholic acid.

V. Porous Drug Matrix Applications

The porous drug matrices described herein are useful in formulations for administration to a patient in need of the drug. As used herein,"patient" refers to animals, including mammals, preferably humans. The formulations deliver a therapeutically or prophylactically effective amount of the drug to the patient.

The porous matrices, or formulations thereof, are suitable for administration of drug by a variety of routes, for example, parenteral, mucosal, oral, topical/transdermal administration, for local, regional, or systemic effect. Examples of parenteral routes include intraveneous, intraarterial, intracardiac, intrathecal, intraosseous, intraarticular, intrasynovial, intracutaneous, subcutaneous, and intramuscular administration. Examples of mucosal routes include pulmonary (intrarespiratory), buccal, sublingual, intranasal, rectal, and vaginal administration. The porous matrices also can be formulated for intraocular, conjunctival, aural, urethral, intracranial, intralesional, and intratumoral administration.

In a preferred embodiment, the drug matrix is in the form of powder, which can be reconstituted with an aqueous medium, such as physiological saline, and administered parenterally, such as intramuscularly, subcutaneously, or intravenously. An advantage of the formulations described herein is that they can be used to convert drugs which must be infused (e.g., to avoid precipitation of the drug following bolus injection) to a bolus formulation, avoiding unacceptable precipitation of drug in vivo or for local delivery.

Alternatively, the matrix can be further processed using standard techniques into tablets or capsules for oral administration, into rectal suppositories, into a dry powder inhaler for pulmonary administration, or mixed/processed into a cream or ointment for topical administration. These standard techniques are described, for example, in Ansel, et al., "Pharmaceutical Dosage Forms and Drug Delivery Systems," 6th Ed., (Williams & Wilkins 1995), which is incorporated herein by reference.

The present invention will be further understood with reference to the following non-limiting examples.

Overview

Examples 1–10 demonstrate production of porous drug matrices using different pore forming agents, different drugs, and different solvents. Examples 1–8 use emulsion formulations to produce the matrices, whereas Examples 9 and 10 use solution formulations to produce the matrices.

Examples 11–13 describe the analyses which were used to characterize the porous drug matrices produced in Examples 1–10. These characteristics include density, drug integrity, and dissolution properties. Example 14 describes particle size analysis and surface area analysis of low water solubility drug particles incorporated into the porous drug matrices.

Examples 15–17 describe experiments demonstrating the increased internal surface area of porous drug matrices produced with pore forming agents. Examples 18–21 describe experiments demonstrating the advantage or need to include a wetting agent as a component of the porous drug matrices.

Example 22 describes an experiment demonstrating the administration of porous drug matrices as an intravenous bolus.

Examples 23 and 24 describe the production of porous drug matrices produced with pore forming agents and pegylated phospholipids.

Materials and Equipment

The following materials and equipment were used in the examples. PEG 3350, PEG 8000, polyvinylpyrrolidone K-15, nifedipine, naproxen, prednisone, SPAN™ 40, lecithin, TWEEN™ 80, PLURONIC™ 127, ammonium chloride, ammonium bicarbonate, and ammonium acetate were obtained from Spectrum Chemicals (Gardena, Calif.). Griseofalvin was obtained from Aldrich Chemicals (Milwaukee, Wis.). Taxol was obtained from Hauser (Boulder, Colo.). 1,2-Dimyristoyl-sn-Glycero-3-Phosphoethanolamine-N-[Poly(ethylene gloycol-5000] (PEG 5000 PE) and 1,2-Dimyristoyl-sn-Glycero-3-Phosphoethanolamine-N-[Poly(ethylene glycol)-2000] (PEG 2000 PE) were obtained from Avanti Polar Lipids Inc. (Alabaster, Ala.). Methylene chloride was obtained from EM Science (Gibbstown, N.J.). All emulsions were produced using a Virtis $IQ^2$ homogenizer (Virtis, Gardiner, N.Y.). Formulations were spray dried on a benchtop spray dryer using an air atomizing nozzle.

EXAMPLE 1

Production of a Porous Prednisone Matrix Using Ammonium Bicarbonate as a Pore Forming Agent with SPAN™ 40 and PEG 8000 as Wetting Agents 5.46 g of PEG 8000, 0.545 g of prednisone, and 0.055 g of SPAN™ 40 were dissolved in 182 mL of methylene chloride. An aqueous solution was prepared by dissolving 3.27 g of ammonium bicarbonate in 18.2 mL of deionized (DI) water. The aqueous solution was added to the organic solution (phase ratio 1:10) and homogenized for 5 minutes at 16,000 RPM. The resulting emulsion was spray dried on a benchtop spray dryer using an air-atomizing nozzle and nitrogen as the drying gas. Spray drying process conditions were 20 ML/min solution flow rate, 60 kg/hr drying gas rate, and 36° C. outlet temperature.

EXAMPLE 2

Production of a Porous Prednisone Matrix Using Ammonium Bicarbonate as a Pore Forming Agent With PEG 8000, TWEEN™ 80, Lecithin as Wetting Agents 5.46 g of PEG 8000, 0.545 g of prednisone, 0.003 g of TWEEN™ 80, and 0.003 g of lecithin were dissolved in 182 mL of methylene chloride. An aqueous solution was prepared as described in Example 1. The aqueous solution was added to the organic solution (phase ratio 1:10) and homogenized for 15 minutes as described in Example 1. The resulting emulsion was spray dried as described in Example 1 using process conditions of 20 mL/min solution flow rate, 60 kg/hr drying gas rate, and 35° C. outlet temperature.

EXAMPLE 3

Production of a Porous Prednisone Matrix Using Ammonium Acetate as a Pore Forming Agent, and PEG 8000, TWEEN™ 80, and Lecithin as Wetting Agents A prednisone-loaded organic solution was prepared as described in Example 2. An aqueous solution was prepared by dissolving 3.27 g of ammonium acetate in 18.2 mL of DI water. The aqueous and organic solutions were homogenized and spray dried as described in Example 2.

EXAMPLE 4

Production of a Porous Prednisone Matrix Using Ammonium Chloride as a Pore Forming Agent, and PEG 8000, TWEEN™ 80, and Lecithin as Wetting Agents A prednisone-loaded organic solution was prepared as described in Example 2. An aqueous solution was prepared by dissolving 3.27 g of ammonium chloride in 18.2 mL of DI water. The aqueous and organic solutions were homogenized as described in Example 1. The resulting emulsion was spray dried as described in Example 2.

EXAMPLE 5

Production of a Porous Griseofulvin Matrix Using Ammonium Bicarbonate as a Pore Forming Agent, and PEG 3350, TWEEN™ 80, and Lecithin as Wetting Agents 9.09 g of PEG 3350, 4.55 g of griseofulvin, 0.01 g of TWEEN™ 80, and 0.01 g of lecithin were dissolved in 182 mL of methylene chloride. An aqueous solution was prepared by dissolving 3.27 g of ammonium bicarbonate and 1.09 g of PEG 3350 in 18.2 mL of DI water. The aqueous and organic solutions were homogenized as described in Example 1. The resulting emulsion was spray dried as described in Example 1 using process conditions of 20 ml/min solution flow rate, 80 kg/hr drying gas rate, and 12° C. outlet temperature.

EXAMPLE 6

Production of a Porous Nifedipine Matrix Using Ammonium Bicarbonate as a Pore Forming Agent, and PEG 3350 and Lecithin as Wetting Agents 9.09 g of PEG 3350, 2.27 g of nifedipine, and 0.009 g of lecithin were dissolved in 182 mL of methylene chloride. An aqueous solution was prepared by dissolving 3.27 g of ammonium bicarbonate in 18.2 mL of DI water. The aqueous and organic solutions were homogenized in described in Example 1. The resulting emulsion was spray dried as described in Example 1 using process conditions of 20 ml/min solution flow rate, 60 kg/hr drying gas rate, and 20° C. outlet temperature.

EXAMPLE 7

Production of a Porous Naproxen Matrix Using Ammonium Chloride as a Pore Forming Agent, and PEG 3350 and Lecithin as Wetting Agents A naproxen-loaded organic solution was prepared by dissolving 10.91 g of PEG 3350, 2.73 g of naproxen, and 0.109 g of lecithin in 182 mL of methylene chloride. An aqueous solution was prepared as described in Example 4. The aqueous and organic solutions were homogenized as described in Example 1, and the resulting emulsion was spray dried using process conditions of 20 m/min solution flow rate, 100 kg/hr drying gas rate, and 20° C. outlet temperature.

EXAMPLE 8

Production of a Porous Paclitaxel Matrix Using Ammonium Bicarbonate as a Pore Forming Agent, and PEG 3350 and Lecithin as Wetting Agents A paclitaxel-loaded organic solution was prepared by dissolving 3.0 g of paclitaxel, 15.0 g of PEG 3350, and 15.7 mg of lecithin in 100 mL of methylene chloride. An aqueous solution composed of 1.8 g of ammonium bicarbonate and, 0.6 g of PEG 3350 in 10 mL of DI water was added to the organic solution (phase ratio 1:10). The mixture was homogenized for 5 minutes at 16,000 RPM. The resulting emulsion was spray dried using process conditions of 10 mL/min solution flow rate, 60 kg/hr drying gas rate, and 25° C. outlet temperature.

EXAMPLE 9

Production of a Porous Nifedipine Matrix Using Ammonium Bicarbonate as a Pore Forming Agent, PEG 3350 and TWEEN™ 80 as Wetting Agents, Polyvinylpyrrolidone as a Bulking Agent, and Ethanol as a Solvent A nifedipine-loaded organic solution was prepared by dissolving 0.76 g of nifedipine, 0.28 g of PEG 3350, and 2.72 g of polyvinylpyrrolidone K-15 in 170 mL of ethanol. An aqueous solution composed of 1.62 g of ammonium bicarbonate and 3 mg of TWEEN™ 80 in 30 mL of DI water was added to the ethanol solution and mixed. The resulting solution was spray dried using process conditions of 20 mL/min solution flow rate, 100 kg/hr drying gas rate, and 36° C. outlet temperature.

EXAMPLE 10

Production of a Porous Nifedipine Matrix Using Ammonium Bicarbonate as a Pore Forming Agent, PEG 3350 and PLURONIC™ F127 as Wetting Agents, Polyvinylpyrrolidone as a Bulking Agent, and Ethanol as a Solvent A nifedipine-loaded organic solution was prepared by dissolving 0.76 g of nifedipine, 0.28 g of PEG 3350, and 2.72 g of polyvinylpyrrolidone K-15 in 170 mL of ethanol. An aqueous solution composed of 1.62 g of ammonium bicarbonate and 3 mg of PLURONIC™ F127 in 30 mL of DI water was added to the ethanol solution and mixed. The resulting solution was spray dried using process conditions of 20 mL/min solution flow rate, 100 kg/hr drying gas rate, and 36° C. outlet temperature.

EXAMPLE 11

In Vitro Dissolution of Porous Drug Matrices

The in vitro dissolution rates of the powders produced in Examples 1–10 were compared to the dissolution rates of the bulk drug of interest.

Analytical Method

All dissolution studies were conducted in PBS (phosphate buffered saline) at room temperature in a glass beaker using overhead mixing. The mixer used was an IKARW16 Basic Mixer with a R1342 impeller shaft running at stirring rate 5. Samples were removed via pipet, filtered through 0.22 micron CA syringe filter, and then analyzed. UV-vis spectroscopy was conducted on an Hewlett Packard Model 8453. Dissolution curves are presented as percent of complete dissolution.

For griseofalvin, PBS (600 mL) was added to an appropriate amount of material being tested to contain 2.4 mg of griseofulvin. UV analysis was performed at 291 nm.

For naproxen, PBS (100 mL) was added to an appropriate amount of material being tested to contain 100 mg of naproxen. All vessels containing naproxen as a solid or as a solution were protected from light. UV analysis was performed at 332 nm.

For nifedipine, PBS (600 mL) was added to an appropriate amount of material being tested to contain 2.4 mg of nifedipine. All vessels containing nifedipine as a solid or in solution were protected from light. UV analysis was performed at 237 nm.

For prednisone, PBS (250 mL) was added to an appropriate amount of material being tested to contain 5 mg of prednisone. UV analysis was performed at 244 nm.

For paclitaxel, studies were conducted in PBS containing 0.08% TWEEN™ 80 (T80/PBS). T80/PBS (10 mL) was added to an appropriate amount of material being tested to contain 5 mg of paclitaxel in a 15 mL polypropylene conical tube, and the suspension was vortexed for 3–4 minutes. The suspension (0.25 mL) was then added to 250 mL of T80/PBS in a 600 mL glass beaker for dissolution analysis. HPLC analysis was performed directly on the filtered aqueous solutions using the paclitaxel HPLC method described in Example 13.

Results

The in vitro dissolution rates of the porous drug matrices produced in examples 1–10 are provided in FIGS. 1–6. The in vitro dissolution of the porous drug matrices are compared to the bulk drug of interest. In all cases, the time for 80% dissolution of the porous drug matrices is 4–50 times shorter than the time for 80% of the bulk drug to dissolve. The rate of dissolution which is approximated as the slope of the curve is 10 to 1400 times greater for the porous drug matrices of Examples 1–10 as compared to the specific bulk drug of interest.

EXAMPLE 12

Density of Porous Drug Matrices

The densities of the dry powder produced in Examples 1–7 are summarized in Table 1. Density was measured using Transaxial Pressure ("TAP") with a Micromeritics GeoPyc 1360 using a consolidation force of 8 Newtons. The matrices are less dense than the starting bulk drug in all cases, indicating that the porous drug matrices are more porous than the commercially available bulk drug.

TABLE 1

Particle Density Analysis

| Material | Density (g/mL) |
| --- | --- |
| Prednisone Bulk | 0.68 |
| Example 1 | 0.48 |
| Example 2 | 0.55 |
| Example 3 | 0.51 |
| Example 4 | 0.49 |
| Griseofulvin Bulk | 0.80 |
| Example 5 | 0.55 |
| Nifedipine Bulk | 1.01 |
| Example 6 | 0.56 |
| Naproxen Bulk | 0.69 |
| Example 7 | 0.58 |

EXAMPLE 13

Integrity of the Drug in Porous Drug Matrices

Analytical Method

Drug integrity post processing was assessed by High Pressure Liquid Chromatography ("HPLC") (Hewlett Packard Series 1100 HPLC). USP chromatography conditions were used for prednisone, naproxen, nifedipine, and griseofulvin. Vessels and vials containing naproxen or nifedipine solutions were protected from light. For paclitaxel, the chromatographic conditions included a Nucleosil column (5:m, C18, 100A, 250×4.6 mm), a mobile phase of 2 mM $H_3PO_4$/Acetonitrile (2:3) at a flow rate of 1.5 mL/min, UV detection at 227 nm, and a run time of 25 min.

Results

The integrities of the drugs following the processing in Examples 1–9 are shown in Table 2 as purities. The process of forming the drug into porous matrices does not appear to alter the purity of the drug.

TABLE 2

Drug Integrity Analysis

| Material | Purity (%) |
| --- | --- |
| Prednisone Powder | 100 |
| Example 1 | 99.8 |
| Example 2 | 99.8 |
| Example 3 | 99.8 |
| Example 4 | 99.8 |
| Griseofulvin Bulk | 95.7 |
| Example 5 | 95.7 |
| Nifedipine Bulk | 100 |
| Example 6 | 100 |
| Example 9 | 100 |
| Example 10 | 100 |
| Naproxen Bulk | 100 |
| Example 7 | 100 |
| Paclitaxel Bulk | 100 |
| Example 8 | 100 |

EXAMPLE 14

Particle Size Analysis and Surface Area Analysis of Drug Particles in Wetted Porous Drug Matrices Analytical Methods Particle size analysis was performed using the Coulter Multisizer II with a 50 micron aperture using siphon mode. Electrolyte was pre-saturated with the drug of interest, and filtered through a 0.22 micron filter prior to addition of lots for analysis to ensure that no portion of the drug within the lot would dissolve during the analysis.

Results

The mean particle size and total surface area of the drug particles generated when the porous drug matrices produced in Examples 1–7 were reconstituted in aqueous media are summarized in Table 3.

TABLE 3

Particle Size and Surface Area Analysis

| Material | Size (microns) | Surface Area ($m^2$/mL of microparticles) |
| --- | --- | --- |
| Prednisone Powder | 2.07 | 1.43 |
| Example 1 | 1.58 | 1.66 |
| Example 2 | 1.39 | 2.53 |
| Example 3 | 1.39 | 3.02 |
| Example 4 | 1.24 | 3.36 |
| Griseofulvin Bulk | 2.42 | 0.88 |
| Example 5 | 2.16 | 1.28 |
| Nifedipine Bulk | 2.64 | 0.57 |

TABLE 3-continued

Particle Size and Surface Area Analysis

| Material | Size (microns) | Surface Area ($m^2$/mL of microparticles) |
|---|---|---|
| Example 6 | 1.78 | 1.98 |
| Naproxen Bulk | 2.89 | 0.66 |
| Example 7 | 1.34 | 2.79 |

In all cases, the particle size of the drug particles which resulted from wetting of the porous drug matrices was reduced relative to the starting bulk material by 10 to 54%, and the total surface area of the particles was increased relative to the starting bulk drug by approximately 16–320%.

EXAMPLE 15

Nifedipine Drug Matrices Containing a Wetting Agent Produced With and Without a Pore Forming Agent A nifedipine/PEG solution was prepared by dissolving 2.0 g of nifedipine, 8.0 g of PEG 3350, and 8 mg of lecithin in 200 mL of methylene chloride (Example 15A). A second identical nifedipine-loaded organic solution was prepared. An aqueous solution composed of 1.8 g of ammonium bicarbonate in 20 mL of DI water was added to the first nifedipine organic solution (phase ratio 1:10). The mixture was homogenized for 5 minutes at 16,000 RPM. The nifedipine solution (Example 15A) and the nifedipine emulsion (Example 15B) were separately spray dried using process conditions of 20 mL/min solution flow rate, 60 kg/hr drying gas rate, and 21° C. outlet temperature.

EXAMPLE 16

Griseofulvin Drug Matrices Containing a Wetting Agent Produced With and Without a Pore Forming Agent A griseofulvin/PEG solution was prepared by dissolving 5.0 g of griseofulvin, 11.2 g of PEG 3350, 11 mg of TWEEN™ 80, and 11 mg of lecithin in 200 mL of methylene chloride (Example 16A). A second identical griseofulvin-loaded organic solution was prepared. An aqueous solution composed of 1.8 g of ammonium bicarbonate in 20 mL of DI water was added to the first organic solution (phase ratio 1:10). The mixture was homogenized for 5 minutes at 16,000 RPM. The griseofulvin solution (Example 16A) and griseofulvin emulsion (Example 16B) were spray dried on a benchtop spray dryer using process conditions of 20 mL/min solution flow rate, 80 kg/hr drying gas rate, and 13° C. outlet temperature.

EXAMPLE 17

Internal Surface Area of Porous Drug Matrices Containing a Wetting Agent and Produced With and Without a Pore Forming Agent The internal surface areas of the drug matrices produced in Examples 15 and 16 were assessed by Krypton BET. BET specific surface area analysis was performed using multipoint surface area analysis with krypton as the gas. Samples were outgassed to 20 micron vacuum at 20° C. prior to analysis.

The results, shown in Table 4, illustrate that the use of the pore forming agent led to an increase of between 2.3 and 3.5 fold in the internal surface area of the resultant drug matrix.

TABLE 4

Internal Surface Area of Drug Matrices

| Matrix (Example No.) | Surface Area ($m^2$/g matrix) |
|---|---|
| Nifedipine with wetting agent (15A) | 0.40 |
| Nifedipine with wetting agent and Ammonium Bicarbonate (15B) | 1.4 |
| Griseofulvin with wetting agent (16A) | 0.41 |
| Griseofulvin with wetting agent and Ammonium Bicarbonate (16B) | 0.95 |

EXAMPLE 18

Nifedipine Drug Matrix Produced Without a Pore Forming Agent or Wetting Agent

A 5% nifedipine solution was prepared by dissolving 10.0 g of nifedipine in 200 mL of methylene chloride. The solution was spray dried on a benchtop spray dryer using the following conditions: 20 mL/min solution flow rate, 60 kg/hr drying gas rate, and 22° C. outlet temperature.

EXAMPLE 19

Griseofulvin Drug Matrix Produced Without a Pore Forming Agent or Wetting Agent

An 8.1% griseofulvin solution was prepared by dissolving 16.2 g of griseofulvin in 200 mL of methylene chloride. The solution was spray dried on a benchtop spray dryer using process conditions of 20 mL/min solution flow rate, 80 kg/hr drying gas rate, and 13° C. outlet temperature.

EXAMPLE 20

Figure 6:
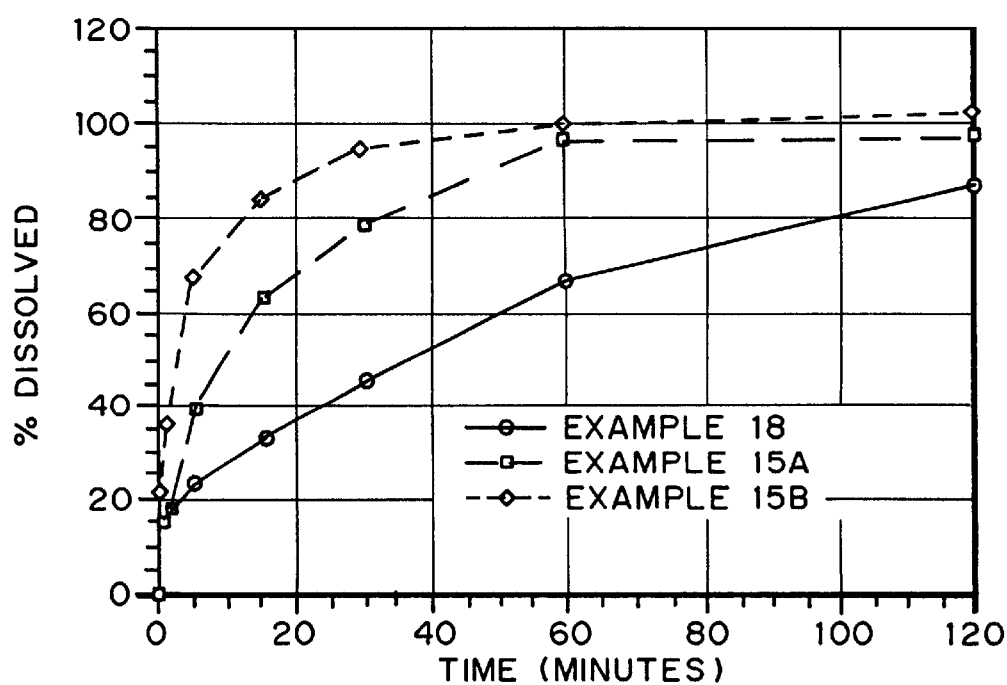
FIG. 6 is a graph of the in vitro dissolution rate (percent dissolved versus time) for various porous matrix forms of nifedipine.

In Vitro Dissolution of Nifedipine Drug Matrices Produced With / Without Pore Forming Agent and Wetting Agent The in vitro dissolution rates of the nifedipine matrices produced in Examples 15 and 18 are shown in FIG. 6. The in vitro dissolution of the drug matrices produced with either wetting agent or wetting agent and pore forming agent have increased dissolution rates as compared to the drug matrix produced with the drug alone. The matrix produced with both the wetting agent and the pore forming agent has the greatest dissolution rate.

EXAMPLE 21

Figure 7:
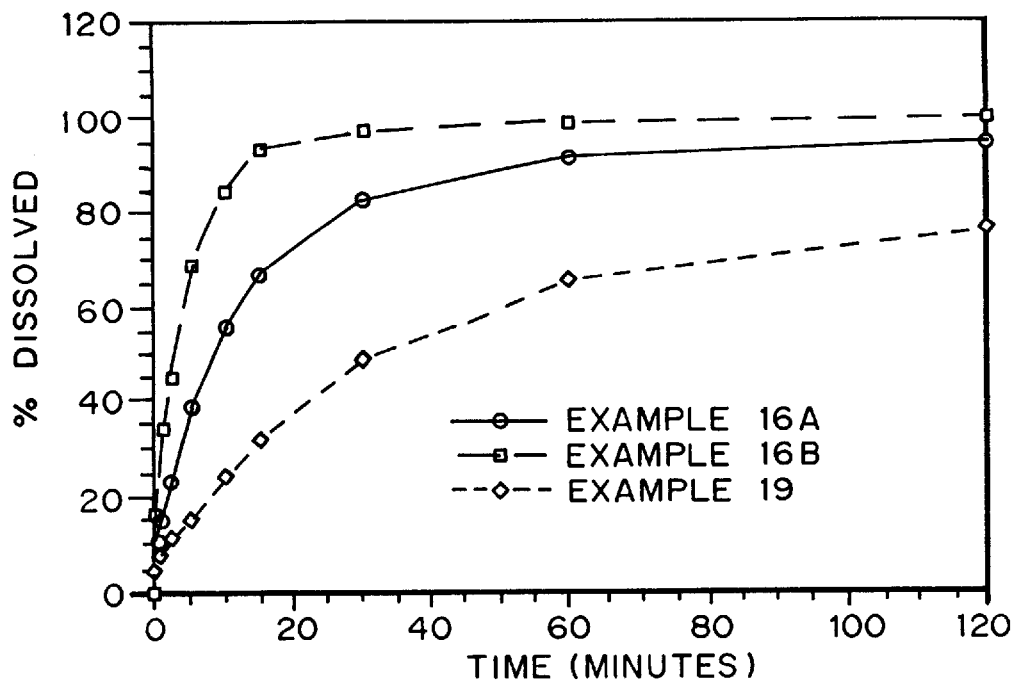
FIG. 7 is a graph of the in vitro dissolution rate (percent dissolved versus time) for various porous matrix forms of griseofulvin.

In Vitro Dissolution of Griseofulvin Drug Matrices Produced With/Without Pore Forming Agent and Wetting Agent The in vitro dissolution rates of the griseofulvin matrices produced in examples 16 and 19 are provided in FIG. 7. The in vitro dissolution of the drug matrices produced with either wetting agent or wetting agent and pore forming agent have increased dissolution rates as compared to the drug matrix produced with the drug alone. The matrix produced with both the wetting agent and the pore forming agent has the greatest dissolution rate.

EXAMPLE 22

Administration of Porous Drug Matrices as an Intravenous Bolus to Dogs

A nifedipine-loaded organic solution was prepared by dissolving 9.09 g of PEG 3350, 2.27 g of nifedipine, and 0.009 g of lecithin in 182 mL of methylene chloride. An aqueous solution was prepared by dissolving 3.27 g of ammonium bicarbonate and 0.91 g of PEG 3350 in 18.2 mL of deionized water at room temperature. The aqueous and organic solutions were homogenized as described in Example 1, and the resulting emulsion was spray dried using process conditions of 20 mL/min solution flow rate, 60 kg/hr drying gas rate, and 20° C. outlet temperature.

A suspension of the porous nifedipine drug matrix was prepared in 5% idextrose solution at a concentration of 2.5 mg/mL. The suspension (2 mL) was administered as a bolus to four beagle dogs, which weighed 8–10 kg. Blood samples were taken at time-points ranging from 1 minute to 24 hours. The samples were processed into plasma, were stored frozen, and were protected from light until analysis via liquid chromatography-mass spectrometry.

Figure 8:
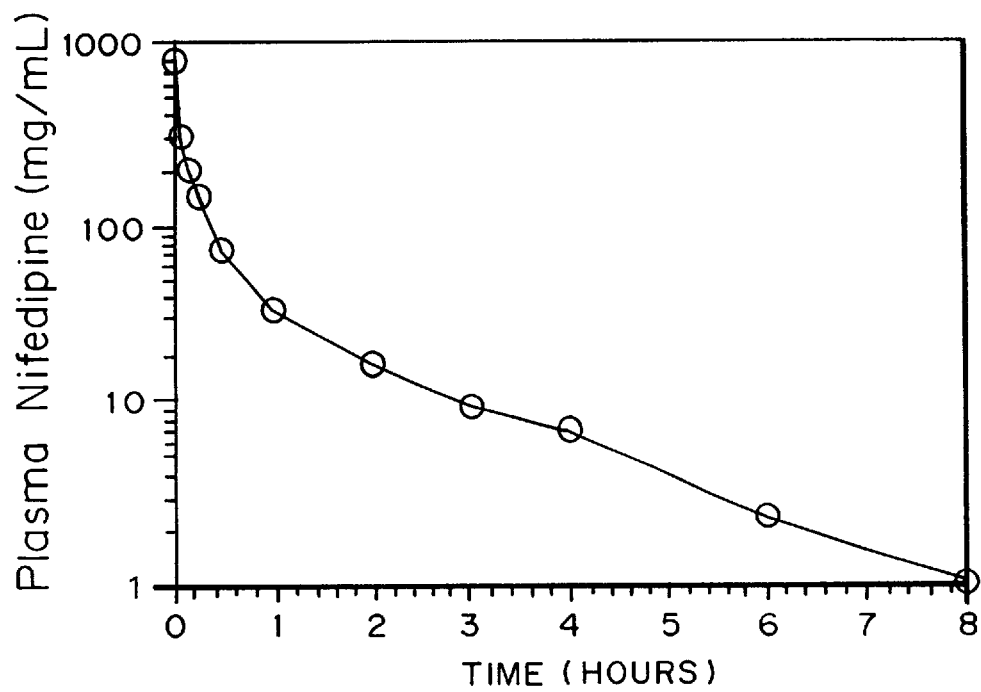
FIG. 8 is a graph of nifedipine plasma levels versus time post intravenous administration of reconstituted nifedipine matrix in dogs.

All animals tolerated the suspension administered as a bolus. The average plasma levels of the intravenously administered suspension is shown in FIG. 8.

EXAMPLE 23

Production of a Porous Nifedipine Matrix Using a Pegylated Phospholipid, 1, 2-Dimyristoyl-sn-Glycero-3 Phosphoethanolamine-N-[Poly(ethylene glycol)-5000 ]

A nifedipine-loaded organic solution was prepared by dissolving 2.0 g of nifedipine, 30.0 g of PEG 3350, 4 mg of lecithin, and 4 mg of 1, 2-Dimyristoylsn-Glycero-3-Phosphoethanolamine-N-[Poly(ethlene glycol)-5000] (PEG 5000 PE) in 202 mL of methylene chloride. An aqueous solution of 1.8 g of ammonium bicarbonate in 20 mL of DI water was added to the organic solution (phase ratio 1:10). The mixture was homogenized for 5 minutes at 16,000 RPM. The resulting emulsion was spray dried using process conditions of 20 mL/min solution flow rate, 60 kg/hr drying gas rate, and 21° C. outlet temperature.

EXAMPLE 24

Production of a Porous Nifedipine Matrix Using a Pegylated Phospholipid, 1, 2-Dimyristoyl-sn-Glycero-3 Phosphoethanolamine-N-[Poly(ethylene glycol)-2000 ]

A nifedipine-loaded organic solution was prepared by dissolving 2.0 g of nifedipine, 30.0 g of PEG 3350, 4 mg of lecithin, and 4 mg of 1, 2-Dimyristoylsn-Glycero-3-Phosphoethanolamine-N-[Poly(ethlene glycol)-2000] (PEG 2000 PE) in 202 mL of methylene chloride. An aqueous solution composed of 1.8 g of ammonium bicarbonate in 20 ml of DI water was added to the organic solution (phase ratio 1:10). The mixture was homogenized for 5 minutes at 16,000 RPM. The resulting emulsion was spray dried using process conditions of 20 mL/min solution flow rate, 60 kg/hr drying gas rate, and 21° C. outlet temperature.

Modifications and variations of the present invention will be obvious to those of skill in the art from the foregoing detailed description. Such modifications and variations are intended to come within the scope of the following claims.

We claim:

1. A method for making a porous matrix of drug comprising
    (a) dissolving a drug in a volatile organic solvent to form a drug solution,
    (b) combining at least one volatile pore forming agent with the volatile organic drug solution to form an emulsion, suspension, or second solution, and
    (c) removing the volatile organic solvent and volatile pore forming agent from the emulsion, suspension, or second solution to yield the porous matrix comprising drug,
    wherein the porous matrix comprising drug has a tap density of less than or equal to 1.0 g/mL or a total surface area of greater than or equal to 0.2 $m^2$/g.

2. The method of claim 1 wherein the drug has low aqueous solubility.

3. The method of claim 1 further comprising incorporating at least one wetting agent into the emulsion, suspension, or second solution.

4. The method of claim 1 wherein step (c) is conducted using a process selected from spray drying, evaporation, fluid bed drying, lyophilization, vacuum drying, or a combination thereof.

5. The method of claim 1 wherein the drug solution or pore forming agent further comprises excipients selected from the group consisting of hydrophilic excipients, pegylated excipients, and tonicity agents.

6. The method of claim 1 wherein the pore forming agent is a volatile salt.

7. The method of claim 1 wherein the volatile salt is selected from the group consisting of ammonium bicarbonate, ammonium acetate, ammonium chloride, ammonium benzoate, and mixtures thereof.

* * * * *

UNITED STATES PATENT AND TRADEMARK OFFICE
CERTIFICATE OF CORRECTION

PATENT NO.    : 6,395,300 B1
DATED         : May 28, 2002
INVENTOR(S)   : Julie Straub et al.

It is certified that error appears in the above-identified patent and that said Letters Patent is hereby corrected as shown below:

Title page,
Item [*] Notice, please delete "This patent is subject to a terminal disclaimer.".

Signed and Sealed this

Sixth Day of September, 2005

JON W. DUDAS
*Director of the United States Patent and Trademark Office*